US012778911B2

(12) United States Patent
Tabuteau

(10) Patent No.: US 12,778,911 B2
(45) Date of Patent: Nov. 3, 2026

(54) COMPOUNDS AND COMBINATIONS THEREOF FOR TREATING NEUROLOGICAL AND PSYCHIATRIC CONDITIONS

(71) Applicant: ANTECIP BIOVENTURES II LLC, New York, NY (US)

(72) Inventor: Herriot Tabuteau, New York, NY (US)

(73) Assignee: ANTECIP BIOVENTURES II LLC, New York, NY (US)

( * ) Notice: Subject to any disclaimer, the term of this patent is extended or adjusted under 35 U.S.C. 154(b) by 0 days.

(21) Appl. No.: 19/446,510

(22) Filed: Jan. 12, 2026

(65) Prior Publication Data

US 2026/0144764 A1 May 28, 2026

Related U.S. Application Data

(63) Continuation of application No. 19/249,959, filed on Jun. 25, 2025, now Pat. No. 12,544,345, which is a continuation of application No. 18/541,574, filed on Dec. 15, 2023, now Pat. No. 12,364,674, which is a continuation of application No. 18/333,944, filed on Jun. 13, 2023, now Pat. No. 11,883,373, which is a continuation of application No. 18/158,268, filed on Jan. 23, 2023, now Pat. No. 11,730,706.

(60) Provisional application No. 63/359,143, filed on Jul. 7, 2022, provisional application No. 63/370,592, filed on Aug. 5, 2022, provisional application No. 63/396,182, filed on Aug. 8, 2022, provisional application No. 63/373,040, filed on Aug. 19, 2022, provisional application No. 63/401,541, filed on Aug. 26, 2022.

(51) Int. Cl.

| | |
|---|---|
| ***A61K 31/137*** | (2006.01) |
| ***A61K 9/20*** | (2006.01) |
| ***A61K 31/135*** | (2006.01) |
| ***A61K 31/4525*** | (2006.01) |
| ***A61K 31/485*** | (2006.01) |
| ***A61P 25/24*** | (2006.01) |
| ***G01N 33/94*** | (2006.01) |

(52) U.S. Cl.

CPC .......... *A61K 31/137* (2013.01); *A61K 9/2009* (2013.01); *A61K 9/2013* (2013.01); *A61K 9/2027* (2013.01); *A61K 9/2054* (2013.01); *A61K 9/2086* (2013.01); *A61K 31/135* (2013.01); *A61K 31/4525* (2013.01); *A61K 31/485* (2013.01); *A61P 25/24* (2018.01); *G01N 33/942* (2013.01); *A61K 9/20* (2013.01); *G01N 2800/52* (2013.01)

(58) Field of Classification Search

CPC ................ A61K 31/137; A61K 31/135; A61K 31/4525; A61K 31/485; A61P 25/24

See application file for complete search history.

(56) References Cited

U.S. PATENT DOCUMENTS

| | | | |
|---|---|---|---|
| 5,358,970 | A | 10/1994 | Ruff et al. |
| 5,731,000 | A | 3/1998 | Ruff et al. |
| 5,763,493 | A | 6/1998 | Ruff et al. |
| 6,306,436 | B1 | 10/2001 | Chungi et al. |
| 6,780,871 | B2 | 8/2004 | Glick et al. |
| 8,088,786 | B2 | 1/2012 | Mckinney et al. |
| 8,569,328 | B1 | 10/2013 | Tabuteau |
| 9,168,234 | B2 | 10/2015 | Tabuteau |
| 9,198,905 | B2 | 12/2015 | Tabuteau |
| 9,205,083 | B2 | 12/2015 | Tabuteau |
| 9,238,032 | B2 | 1/2016 | Tabuteau |
| 9,278,095 | B2 | 3/2016 | Tabuteau |
| 9,314,462 | B2 | 4/2016 | Tabuteau |
| 9,370,513 | B2 | 6/2016 | Tabuteau |
| 9,375,429 | B2 | 6/2016 | Tabuteau |
| 9,402,843 | B2 | 8/2016 | Tabuteau |
| 9,402,844 | B2 | 8/2016 | Tabuteau |

(Continued)

FOREIGN PATENT DOCUMENTS

| | | | |
|---|---|---|---|
| BR | 102016010170 | A2 | 11/2017 |
| EP | 4183391 | A1 | 5/2023 |

(Continued)

OTHER PUBLICATIONS

Ward et all., "AXS-05: an investigational treatment for Alzheimer's disease-associated agitation", Expert Opinion On Investigational Drugs, vol. 31, No. 8, pp. 773-780. (Year: 2022).*

(Continued)

*Primary Examiner* — Kevin E Weddington

(74) *Attorney, Agent, or Firm* — PROCOPIO, CORY, HARGREAVES & SAVITCH LLP; Brent Johnson; Yuefen Zhou

(57) ABSTRACT

This disclosure relates to administration of a combination of: 1) about 100-110 mg, about 104-106 mg, or about 105 mg of bupropion hydrochloride, or a molar equivalent amount of the free base form or another salt form of bupropion; and 2) about 40-50 mg, about 44-46 mg, or about 45 mg of dextromethorphan hydrobromide, or a molar equivalent amount of the free base form or another salt form of dextromethorphan in certain patient populations, such as patients having moderate renal impairment, patients receiving a concomitant strong CYP2D6 inhibitor, patients who are known CYP2D6 poor metabolizers, those in need of an NMDA antagonist that does not cause dissociation, and those at risk of QT prolongation.

20 Claims, 3 Drawing Sheets

(56) References Cited

U.S. PATENT DOCUMENTS

| | | | | |
|---|---|---|---|---|
| 9,408,815 | B2 | 8/2016 | Tabuteau | |
| 9,421,176 | B1 | 8/2016 | Tabuteau | |
| 9,457,023 | B1 | 10/2016 | Tabuteau | |
| 9,457,025 | B2 | 10/2016 | Tabuteau | |
| 9,474,731 | B1 | 10/2016 | Tabuteau | |
| 9,486,450 | B2 | 11/2016 | Tabuteau | |
| 9,700,528 | B2 | 7/2017 | Tabuteau | |
| 9,700,553 | B2 | 7/2017 | Tabuteau | |
| 9,707,191 | B2 | 7/2017 | Tabuteau | |
| 9,763,932 | B2 | 9/2017 | Tabuteau | |
| 9,861,595 | B2 | 1/2018 | Tabuteau | |
| 9,867,819 | B2 | 1/2018 | Tabuteau | |
| 9,968,568 | B2 | 5/2018 | Tabuteau | |
| 10,058,518 | B2 | 8/2018 | Tabuteau | |
| 10,064,857 | B2 | 9/2018 | Tabuteau | |
| 10,080,727 | B2 | 9/2018 | Tabuteau | |
| 10,092,560 | B2 | 10/2018 | Tabuteau | |
| 10,092,561 | B2 | 10/2018 | Tabuteau | |
| 10,105,327 | B2 | 10/2018 | Tabuteau | |
| 10,105,361 | B2 | 10/2018 | Tabuteau | |
| 10,251,879 | B2 | 4/2019 | Tabuteau | |
| 10,463,634 | B2 | 11/2019 | Tabuteau | |
| 10,512,643 | B2 | 12/2019 | Tabuteau | |
| 10,548,857 | B2 | 2/2020 | Tabuteau | |
| 10,596,167 | B2 | 3/2020 | Tabuteau | |
| 10,688,066 | B2 | 6/2020 | Tabuteau | |
| 10,695,304 | B2 | 6/2020 | Tabuteau | |
| 10,772,850 | B2 | 9/2020 | Tabuteau | |
| 10,780,064 | B2 | 9/2020 | Tabuteau | |
| 10,780,066 | B2 | 9/2020 | Tabuteau | |
| 10,786,469 | B2 | 9/2020 | Tabuteau | |
| 10,786,496 | B2 | 9/2020 | Tabuteau | |
| 10,799,497 | B2 | 10/2020 | Tabuteau | |
| 10,806,710 | B2 | 10/2020 | Tabuteau | |
| 10,813,924 | B2 | 10/2020 | Tabuteau | |
| 10,864,209 | B2 | 12/2020 | Tabuteau | |
| 10,874,663 | B2 | 12/2020 | Tabuteau | |
| 10,874,664 | B2 | 12/2020 | Tabuteau | |
| 10,874,665 | B2 | 12/2020 | Tabuteau | |
| 10,881,624 | B2 | 1/2021 | Tabuteau | |
| 10,881,657 | B2 | 1/2021 | Tabuteau | |
| 10,894,046 | B2 | 1/2021 | Tabuteau | |
| 10,894,047 | B2 | 1/2021 | Tabuteau | |
| 10,898,453 | B2 | 1/2021 | Tabuteau | |
| 10,925,842 | B2 | 2/2021 | Tabuteau | |
| 10,933,034 | B2 | 3/2021 | Tabuteau | |
| 10,940,124 | B2 | 3/2021 | Tabuteau | |
| 10,945,973 | B2 | 3/2021 | Tabuteau | |
| 10,966,941 | B2 | 4/2021 | Tabuteau | |
| 10,966,942 | B2 | 4/2021 | Tabuteau | |
| 10,966,974 | B2 | 4/2021 | Tabuteau | |
| 10,980,800 | B2 | 4/2021 | Tabuteau | |
| 11,007,189 | B2 | 5/2021 | Tabuteau | |
| 11,020,389 | B2 | 6/2021 | Tabuteau | |
| 11,058,648 | B2 | 7/2021 | Tabuteau | |
| 11,066,248 | B2 | 7/2021 | Tabuteau | |
| 11,090,300 | B2 | 8/2021 | Tabuteau | |
| 11,096,937 | B2 | 8/2021 | Tabuteau | |
| 11,123,343 | B2 | 9/2021 | Tabuteau | |
| 11,123,344 | B2 | 9/2021 | Tabuteau | |
| 11,129,826 | B2 | 9/2021 | Tabuteau | |
| 11,141,388 | B2 | 10/2021 | Tabuteau | |
| 11,141,416 | B2 | 10/2021 | Tabuteau | |
| 11,147,808 | B2 | 10/2021 | Tabuteau | |
| 11,185,515 | B2 | 11/2021 | Tabuteau | |
| 11,191,739 | B2 | 12/2021 | Tabuteau | |
| 11,197,839 | B2 | 12/2021 | Tabuteau | |
| 11,207,281 | B2 | 12/2021 | Tabuteau | |
| 11,213,521 | B2 | 1/2022 | Tabuteau | |
| 11,229,640 | B2 | 1/2022 | Tabuteau | |
| 11,234,946 | B2 | 2/2022 | Tabuteau | |
| 11,253,491 | B2 | 2/2022 | Tabuteau | |
| 11,253,492 | B2 | 2/2022 | Tabuteau | |
| 11,273,133 | B2 | 3/2022 | Tabuteau | |
| 11,273,134 | B2 | 3/2022 | Tabuteau | |
| 11,285,118 | B2 | 3/2022 | Tabuteau | |
| 11,285,146 | B2 | 3/2022 | Tabuteau | |
| 11,291,638 | B2 | 4/2022 | Tabuteau | |
| 11,291,665 | B2 | 4/2022 | Tabuteau | |
| 11,298,351 | B2 | 4/2022 | Tabuteau | |
| 11,298,352 | B2 | 4/2022 | Tabuteau | |
| 11,311,534 | B2 | 4/2022 | Tabuteau | |
| 11,344,544 | B2 | 5/2022 | Tabuteau | |
| 11,357,744 | B2 | 6/2022 | Tabuteau | |
| 11,364,233 | B2 | 6/2022 | Tabuteau | |
| 11,382,874 | B2 | 7/2022 | Tabuteau | |
| 11,419,867 | B2 | 8/2022 | Tabuteau | |
| 11,426,370 | B2 | 8/2022 | Tabuteau | |
| 11,426,401 | B2 | 8/2022 | Tabuteau | |
| 11,433,067 | B2 | 9/2022 | Tabuteau | |
| 11,439,636 | B1 | 9/2022 | Tabuteau | |
| 11,478,468 | B2 | 10/2022 | Tabuteau | |
| 11,497,721 | B2 | 11/2022 | Tabuteau | |
| 11,510,918 | B2 | 11/2022 | Tabuteau | |
| 11,517,542 | B2 | 12/2022 | Tabuteau | |
| 11,517,543 | B2 | 12/2022 | Tabuteau | |
| 11,517,544 | B2 | 12/2022 | Tabuteau | |
| 11,524,007 | B2 | 12/2022 | Tabuteau | |
| 11,524,008 | B2 | 12/2022 | Tabuteau | |
| 11,534,414 | B2 | 12/2022 | Tabuteau | |
| 11,541,021 | B2 | 1/2023 | Tabuteau | |
| 11,541,048 | B2 | 1/2023 | Tabuteau | |
| 11,571,399 | B2 | 2/2023 | Tabuteau | |
| 11,571,417 | B2 | 2/2023 | Tabuteau | |
| 11,576,877 | B2 | 2/2023 | Tabuteau | |
| 11,576,909 | B2 | 2/2023 | Tabuteau | |
| 11,590,124 | B2 | 2/2023 | Tabuteau | |
| 11,596,627 | B2 | 3/2023 | Tabuteau | |
| 11,617,728 | B2 | 4/2023 | Tabuteau | |
| 11,617,747 | B2 | 4/2023 | Tabuteau | |
| 11,628,149 | B2 | 4/2023 | Tabuteau | |
| 11,660,273 | B2 | 5/2023 | Tabuteau | |
| 11,660,274 | B2 | 5/2023 | Tabuteau | |
| 11,717,518 | B1 | 8/2023 | Tabuteau | |
| 11,730,706 | B1 | 8/2023 | Tabuteau | |
| 11,752,144 | B1 | 9/2023 | Tabuteau | |
| 11,779,579 | B2 | 10/2023 | Tabuteau | |
| 11,839,612 | B1 | 12/2023 | Tabuteau | |
| 11,844,797 | B1 | 12/2023 | Tabuteau | |
| 11,883,373 | B1 | 1/2024 | Tabuteau | |
| 11,896,563 | B2 | 2/2024 | Tabuteau | |
| 11,925,636 | B2 | 3/2024 | Tabuteau | |
| 11,969,421 | B2 | 4/2024 | Tabuteau | |
| 11,986,444 | B2 | 5/2024 | Tabuteau | |
| 12,036,191 | B1 | 7/2024 | Tabuteau | |
| 12,042,473 | B2 | 7/2024 | Tabuteau | |
| 12,109,178 | B2 | 10/2024 | Tabuteau | |
| 12,138,260 | B2 | 11/2024 | Tabuteau | |
| 12,146,889 | B1 | 11/2024 | Tabuteau | |
| 12,156,914 | B2 | 12/2024 | Tabuteau | |
| 12,194,005 | B2 | 1/2025 | Tabuteau | |
| 12,194,006 | B2 | 1/2025 | Tabuteau | |
| 12,194,036 | B2 * | 1/2025 | Tabuteau | A61K 9/209 |
| 12,239,642 | B2 | 3/2025 | Tabuteau | |
| 12,263,161 | B2 * | 4/2025 | Tabuteau | A61K 31/138 |
| 12,310,961 | B2 | 5/2025 | Tabuteau | |
| 12,364,674 | B2 * | 7/2025 | Tabuteau | A61K 31/137 |
| 12,370,154 | B2 * | 7/2025 | Tabuteau | A61K 31/137 |
| 12,377,091 | B2 | 8/2025 | Tabuteau | |
| 12,390,428 | B2 | 8/2025 | Tabuteau | |
| 12,433,884 | B2 | 10/2025 | Tabuteau | |
| 12,447,138 | B2 | 10/2025 | Tabuteau | |
| 12,472,155 | B2 | 11/2025 | Tabuteau | |
| 12,472,156 | B2 | 11/2025 | Tabuteau | |
| 12,472,174 | B2 | 11/2025 | Tabuteau | |
| 12,478,622 | B2 | 11/2025 | Tabuteau | |
| 12,544,345 | B2 * | 2/2026 | Tabuteau | A61K 31/485 |
| 12,564,587 | B2 | 3/2026 | Tabuteau | |
| 12,569,479 | B2 | 3/2026 | Tabuteau | |
| 12,576,078 | B1 | 3/2026 | Tabuteau | |
| 12,599,576 | B2 | 4/2026 | Tabuteau | |
| 2002/0035105 | A1 | 3/2002 | Caruso | |
| 2003/0044462 | A1 | 3/2003 | Subramanian et al. | |
| 2008/0044462 | A1 | 2/2008 | Trumbore et al. | |

(56) References Cited

U.S. PATENT DOCUMENTS

2010/0040679 A1 2/2010 Chang
2010/0291225 A1 11/2010 Fanda et al.
2015/0126541 A1 5/2015 Tabuteau
2015/0126542 A1 5/2015 Tabuteau
2015/0126543 A1 5/2015 Tabuteau
2015/0126544 A1 5/2015 Tabuteau
2015/0133485 A1 5/2015 Tabuteau
2015/0133486 A1 5/2015 Tabuteau
2015/0150830 A1 6/2015 Tabuteau
2015/0157582 A1 6/2015 Tabuteau
2015/0342947 A1 12/2015 Pollard et al.
2016/0008352 A1 1/2016 Tabuteau
2016/0030420 A1 2/2016 Tabuteau
2016/0030421 A1 2/2016 Tabuteau
2016/0128944 A1 5/2016 Chawrai et al.
2016/0128998 A1 5/2016 Tabuteau
2016/0136155 A1 5/2016 Tabuteau
2016/0199321 A1 7/2016 Tabuteau
2016/0228390 A1 8/2016 Tabuteau
2016/0263099 A1 9/2016 Tabuteau
2016/0263100 A1 9/2016 Tabuteau
2016/0317475 A1 11/2016 Tabuteau
2016/0317476 A1 11/2016 Tabuteau
2016/0324807 A1 11/2016 Tabuteau
2016/0339017 A1 11/2016 Tabuteau
2016/0346276 A1 12/2016 Tabuteau
2016/0361305 A1 12/2016 Tabuteau
2016/0375008 A1 12/2016 Tabuteau
2016/0375012 A1 12/2016 Tabuteau
2017/0007558 A1 1/2017 Tabuteau
2017/0014357 A1 1/2017 Tabuteau
2017/0252309 A1 9/2017 Tabuteau
2017/0281617 A1 10/2017 Tabuteau
2017/0304229 A1 10/2017 Tabuteau
2017/0304230 A1 10/2017 Tabuteau
2017/0304298 A1 10/2017 Tabuteau
2017/0354619 A1 12/2017 Tabuteau
2017/0360773 A1 12/2017 Tabuteau
2017/0360774 A1 12/2017 Tabuteau
2017/0360776 A1 12/2017 Tabuteau
2018/0092906 A1 4/2018 Tabuteau
2018/0116980 A1 5/2018 Tabuteau
2018/0133195 A1 5/2018 Tabuteau
2018/0207151 A1 7/2018 Tabuteau
2018/0256518 A1 9/2018 Tabuteau
2018/0360823 A1 12/2018 Tabuteau
2019/0000835 A1 1/2019 Tabuteau
2019/0008800 A1 1/2019 Tabuteau
2019/0008801 A1 1/2019 Tabuteau
2019/0008805 A1 1/2019 Tabuteau
2019/0015407 A1 1/2019 Tabuteau
2019/0083426 A1 3/2019 Tabuteau
2019/0142768 A1 5/2019 Tabuteau
2019/0192450 A1 6/2019 Tabuteau
2019/0192507 A1 6/2019 Tabuteau
2019/0216798 A1 7/2019 Tabuteau
2019/0216800 A1 7/2019 Tabuteau
2019/0216801 A1 7/2019 Tabuteau
2019/0290601 A1 9/2019 Tabuteau
2020/0022929 A1 1/2020 Tabuteau
2020/0093762 A1 3/2020 Tabuteau
2020/0147008 A1 5/2020 Tabuteau
2020/0147075 A1 5/2020 Tabuteau
2020/0206217 A1 7/2020 Tabuteau
2020/0215055 A1 7/2020 Tabuteau
2020/0215056 A1 7/2020 Tabuteau
2020/0215057 A1 7/2020 Tabuteau
2020/0215058 A1 7/2020 Tabuteau
2020/0215059 A1 7/2020 Tabuteau
2020/0222389 A1 7/2020 Tabuteau
2020/0230078 A1 7/2020 Tabuteau
2020/0230129 A1 7/2020 Tabuteau
2020/0230130 A1 7/2020 Tabuteau
2020/0230131 A1 7/2020 Tabuteau
2020/0237751 A1 7/2020 Tabuteau
2020/0237752 A1 7/2020 Tabuteau
2020/0246280 A1 8/2020 Tabuteau
2020/0261431 A1 8/2020 Tabuteau
2020/0297666 A1 9/2020 Tabuteau
2020/0338022 A1 10/2020 Tabuteau
2020/0360310 A1 11/2020 Tabuteau
2020/0397723 A1 12/2020 Tabuteau
2020/0397724 A1 12/2020 Tabuteau
2020/0405664 A1 12/2020 Tabuteau
2021/0000763 A1 1/2021 Tabuteau
2021/0000764 A1 1/2021 Tabuteau
2021/0000765 A1 1/2021 Tabuteau
2021/0000768 A1 1/2021 Tabuteau
2021/0000820 A1 1/2021 Tabuteau
2021/0015768 A1 1/2021 Tabuteau
2021/0015814 A1 1/2021 Tabuteau
2021/0015815 A1 1/2021 Tabuteau
2021/0023075 A1 1/2021 Tabuteau
2021/0023076 A1 1/2021 Tabuteau
2021/0030747 A1 2/2021 Tabuteau
2021/0030749 A1 2/2021 Tabuteau
2021/0030750 A1 2/2021 Tabuteau
2021/0030751 A1 2/2021 Tabuteau
2021/0046067 A1 2/2021 Tabuteau
2021/0052521 A1 2/2021 Tabuteau
2021/0060004 A1 3/2021 Tabuteau
2021/0060005 A1 3/2021 Tabuteau
2021/0069125 A1 3/2021 Tabuteau
2021/0069128 A1 3/2021 Tabuteau
2021/0077428 A1 3/2021 Tabuteau
2021/0077429 A1 3/2021 Tabuteau
2021/0077483 A1 3/2021 Tabuteau
2021/0106546 A1 4/2021 Tabuteau
2021/0177834 A1 6/2021 Tabuteau
2021/0186899 A1 6/2021 Tabuteau
2021/0186900 A1 6/2021 Tabuteau
2021/0186901 A1 6/2021 Tabuteau
2021/0186955 A1 6/2021 Tabuteau
2021/0186956 A1 6/2021 Tabuteau
2021/0196704 A1 7/2021 Tabuteau
2021/0196705 A1 7/2021 Tabuteau
2021/0205239 A1 7/2021 Tabuteau
2021/0205240 A1 7/2021 Tabuteau
2021/0205297 A1 7/2021 Tabuteau
2021/0220293 A1 7/2021 Tabuteau
2021/0220294 A1 7/2021 Tabuteau
2021/0220348 A1 7/2021 Tabuteau
2021/0260054 A1 8/2021 Tabuteau
2021/0267967 A1 9/2021 Tabuteau
2021/0338605 A1 11/2021 Tabuteau
2021/0346370 A1 11/2021 Tabuteau
2021/0361645 A1 11/2021 Tabuteau
2021/0401828 A1 12/2021 Tabuteau
2021/0401829 A1 12/2021 Tabuteau
2021/0401830 A1 12/2021 Tabuteau
2021/0401831 A1 12/2021 Tabuteau
2022/0008363 A1 1/2022 Tabuteau
2022/0071930 A1 3/2022 Tabuteau
2022/0071931 A1 3/2022 Tabuteau
2022/0079892 A1 3/2022 Tabuteau
2022/0096462 A1 3/2022 Tabuteau
2022/0105086 A1 4/2022 Tabuteau
2022/0133655 A1 5/2022 Tabuteau
2022/0142950 A1 5/2022 Tabuteau
2022/0193012 A1 6/2022 Tabuteau
2022/0218631 A1 7/2022 Tabuteau
2022/0218698 A1 7/2022 Tabuteau
2022/0233470 A1 7/2022 Tabuteau
2022/0233474 A1 7/2022 Tabuteau
2022/0233518 A1 7/2022 Tabuteau
2022/0233519 A1 7/2022 Tabuteau
2022/0241220 A1 8/2022 Tabuteau
2022/0241221 A1 8/2022 Tabuteau
2022/0241269 A1 8/2022 Tabuteau
2022/0241270 A1 8/2022 Tabuteau
2022/0265639 A1 8/2022 Tabuteau
2022/0280504 A1 9/2022 Tabuteau
2022/0313689 A1 10/2022 Tabuteau
2022/0323381 A1 10/2022 Tabuteau

(56) References Cited

U.S. PATENT DOCUMENTS

| | | | |
|---|---|---|---|
| 2022/0378779 | A1 | 12/2022 | Tabuteau |
| 2023/0045675 | A1 | 2/2023 | Tabuteau |
| 2023/0096437 | A1 | 3/2023 | Tabuteau |
| 2023/0099206 | A1 | 3/2023 | Tabuteau |
| 2023/0100008 | A1 | 3/2023 | Tabuteau |
| 2023/0100913 | A1 | 3/2023 | Tabuteau |
| 2023/0114111 | A1 | 4/2023 | Tabuteau |
| 2023/0131854 | A1 | 4/2023 | Tabuteau |
| 2023/0142244 | A1 | 5/2023 | Tabuteau |
| 2023/0210843 | A1 | 7/2023 | Tabuteau |
| 2023/0218550 | A1 | 7/2023 | Tabuteau |
| 2023/0225995 | A1 | 7/2023 | Tabuteau |
| 2023/0233491 | A1 | 7/2023 | Tabuteau |
| 2023/0241010 | A1 | 8/2023 | Tabuteau |
| 2023/0248668 | A1 | 8/2023 | Tabuteau |
| 2023/0248669 | A1 | 8/2023 | Tabuteau |
| 2023/0263750 | A1 | 8/2023 | Tabuteau |
| 2023/0265905 | A1 | 8/2023 | Tabuteau |
| 2023/0270740 | A1 | 8/2023 | Tabuteau |
| 2023/0277478 | A1 | 9/2023 | Tabuteau |
| 2023/0277479 | A1 | 9/2023 | Tabuteau |
| 2023/0277480 | A1 | 9/2023 | Tabuteau |
| 2023/0277481 | A1 | 9/2023 | Tabuteau |
| 2023/0277504 | A1 | 9/2023 | Tabuteau |
| 2023/0293456 | A1 | 9/2023 | Tabuteau |
| 2024/0000770 | A1 | 1/2024 | Tabuteau |
| 2024/0016797 | A1 | 1/2024 | Tabuteau |
| 2024/0024309 | A1 | 1/2024 | Tabuteau |
| 2024/0041862 | A1 | 2/2024 | Tabuteau |
| 2024/0041863 | A1 | 2/2024 | Tabuteau |
| 2024/0050383 | A1 | 2/2024 | Tabuteau |
| 2024/0066025 | A1 | 2/2024 | Tabuteau |
| 2024/0115524 | A1 | 4/2024 | Tabuteau |
| 2024/0148719 | A1 | 5/2024 | Tabuteau |
| 2024/0156751 | A1 | 5/2024 | Tabuteau |
| 2024/0165104 | A1 | 5/2024 | Tabuteau |
| 2024/0189302 | A1 | 6/2024 | Tabuteau |
| 2024/0197656 | A1 | 6/2024 | Tabuteau |
| 2024/0197720 | A1 | 6/2024 | Tabuteau |
| 2024/0238276 | A1 | 7/2024 | Tabuteau |
| 2024/0252451 | A1 | 8/2024 | Tabuteau |
| 2024/0269130 | A1 | 8/2024 | Tabuteau |
| 2024/0299319 | A1 | 9/2024 | Tabuteau |
| 2024/0299320 | A1 | 9/2024 | Tabuteau |
| 2024/0307408 | A1 | 9/2024 | Tabuteau |
| 2024/0390297 | A1 | 11/2024 | Tabuteau |
| 2024/0408040 | A1 | 12/2024 | Tabuteau |
| 2025/0009754 | A1 | 1/2025 | Tabuteau |
| 2025/0012821 | A1 | 1/2025 | Tabuteau |
| 2025/0025458 | A1 | 1/2025 | Tabuteau |
| 2025/0032432 | A1 | 1/2025 | Tabuteau |
| 2025/0064797 | A1 | 2/2025 | Tabuteau |
| 2025/0073188 | A1 | 3/2025 | Tabuteau |
| 2025/0090521 | A1 | 3/2025 | Tabuteau |
| 2025/0177380 | A1 | 6/2025 | Tabuteau |
| 2025/0186428 | A1 | 6/2025 | Tabuteau |
| 2025/0241907 | A1 | 7/2025 | Tabuteau |
| 2025/0262175 | A1 | 8/2025 | Tabuteau |
| 2025/0268890 | A1 | 8/2025 | Tabuteau |
| 2025/0268891 | A1 | 8/2025 | Tabuteau |
| 2025/0281430 | A1 | 9/2025 | Tabuteau |
| 2025/0302969 | A1 | 10/2025 | Tabuteau |
| 2025/0319043 | A1 | 10/2025 | Tabuteau |
| 2025/0325539 | A1 | 10/2025 | Tabuteau |
| 2025/0332123 | A1 | 10/2025 | Tabuteau |
| 2025/0339538 | A1 | 11/2025 | Tabuteau |
| 2025/0345294 | A1 | 11/2025 | Tabuteau |
| 2025/0367142 | A1 | 12/2025 | Tabuteau |
| 2026/0041651 | A1 | 2/2026 | Tabuteau |
| 2026/0048129 | A1 | 2/2026 | Tabuteau |
| 2026/0053758 | A1 | 2/2026 | Tabuteau |
| 2026/0060976 | A1 | 3/2026 | Tabuteau |
| 2026/0097006 | A1 | 4/2026 | Tabuteau |

FOREIGN PATENT DOCUMENTS

| | | | |
|---|---|---|---|
| KR | 101612197 | B1 | 4/2016 |
| WO | 1998050044 | | 11/1998 |
| WO | 2003086362 | A2 | 10/2003 |
| WO | 2004089873 | A1 | 10/2004 |
| WO | 2009006194 | | 1/2009 |
| WO | 2009050726 | A2 | 4/2009 |
| WO | 2015069809 | A1 | 5/2015 |
| WO | 2016125108 | A1 | 8/2016 |
| WO | 2019165379 | A1 | 8/2019 |
| WO | 2020146412 | A1 | 7/2020 |
| WO | 2021202329 | A1 | 10/2021 |
| WO | 2021202419 | A1 | 10/2021 |
| WO | 2022119981 | A1 | 6/2022 |
| WO | 2023004064 | A1 | 1/2023 |
| WO | 2023019138 | A1 | 2/2023 |
| WO | 2023225511 | A1 | 11/2023 |
| WO | 2024006812 | A1 | 1/2024 |
| WO | 2024006853 | A1 | 1/2024 |
| WO | 2024011138 | A1 | 1/2024 |
| WO | 2024118570 | A1 | 6/2024 |

OTHER PUBLICATIONS

Xue et al., "Prediction of Drug-Drug Interactions with Bupropion and Its Metabolites as CY2D6 Inhibitors Using a Physiologically-Based Pharmacokinetic Model", Pharmaceutics, vol. 10, No. 1, pp. 1-20 (2018).*

Goodnick, Psychotropic drugs and the ECG: focus on the QTc interval, Expert Opinion on Pharmacotherapy, vol. 3, No. 5, p. 479-498, 2002.

International Search Report and Written Opinion, PCT/US2024/046359 mailed on Nov. 28, 2024.

Tabuteau H, et al. "Effect of AXS-05 (Dextromethorphan-Bupropion) in Major Depressive Disorder: A Randomized Double-Blind Controlled Trial" Am J Psychiatry (2022) vol. 179 pp. 490-499. doi: 10.1176/appi.ajp.21080800.

International Preliminary Report on Patentability, PCT/US2023/067062, mailed on Nov. 28, 2024.

International Search Report and Written Opinion, PCT/US2024/043903 mailed on Nov. 28, 2024.

International Preliminary Report on Patentability, PCT/US2023/069286, mailed on Jan. 9, 2025.

International Preliminary Report on Patentability, PCT/US2023/069371, mailed on Jan. 9, 2025.

International Preliminary Report on Patentability, PCT/US2023/069655, mailed on Jan. 16, 2025.

Kotlyar et al., Effect of bupropion on physiological measures of stress in smokers during nicotine withdrawal, Pharmacology Biochemistry and Behavior, vol. 83, Issue 3, Mar. 2006, pp. 370-379. [https://doi.org/10.1016/j.pbb.2006.02.017].

International Search Report and Written Opinion, PCT/US2025/016339 mailed on Apr. 3, 2025.

Surovik, J.; et al. "A case of bupropion-induced Stevens-Johnson syndrome with acute psoriatic exacerbation," J. Drugs Dermatol. Aug. 2010, 9(8), 1010-1012. [Abstract].

Garcia, M.; et al. "Eosinophilia associated with bupropion," Int. J. Clin. Pharm. 2013, 35, 532-534. DOI: 10.1007/s11096-013-9803-y. [Abstract].

Ketenci, M.; et al. "Toxic Twist: A Case of Bupropion Induced Brugada Syndrome," Circulation 2023, 148, 1, Abstract 15984. DOI: 10.1161/circ.148.suppl_1.15984. [Abstract].

Ray, A.K.; et al. "Bupropion-Induced Acute Generalized Exanthematous Pustulosis," Pharmacotherapy 2012, 31(6). 621. DOI: 10.1592/phco.31.6.621. [Abstract].

Akbar, D.; et al. "Dextromethorphan-Bupropion for the Treatment of Depression: A Systematic Review of Efficacy and Safety in Clinical Trials," CNS Drugs 2023, 37(10), 867-881. DOI: 10.1007/s40263-023-01032-5. [Abstract].

Mccarthy B.; et al. "Dextromethorphan-bupropion (Auvelity) for the Treatment of Major Depressive Disorder," Clin. Psychopharmacol. Neurosci. 2023, 21(4), 609-616. DOI: 10.9758/cpn.23.1081.

(56) References Cited

OTHER PUBLICATIONS

Axsome Therapeutics, Inc. "A Trial of AXS-05 in Patients With Major Depressive Disorder (GEMINI)," Clinicaltrials.gov, NCT04019704 version 8, Sep. 16, 2022.
International Search Report and Written Opinion of the International Searching Authority for PCT/US25/30642, mailed on Jun. 18, 2026.
Iosifescu D. V. et al.: "Efficacy and Safety of AXS-05 (Dextromethorphan-Bupropion) in Patients With Major Depressive Disorder—A Phase 3 Randomized Clinical Trial (GEMINI)", Journal of Clinical Psychiatry, 2022, vol. 83, No. 4, article 2lml4345, 9 pages. [DOI: 10.4088/JCP.2lml4345].
Axsome Therapeutics, Inc.: "A Study to Assess the Efficacy and Safety of AXS-05 in Subjects With Treatment Resistant Major Depressive Disorder (STRIDE-I )", ClinicalTrials.gov, NCT02741791, update of Mar. 24, 2021.
Axsome Therapeutics. Inc.: "Open-Label Safely Study of AXS-05 in Subjects With TRD (Evolve)", ClinicalTrials.gov. NCT04634669, update of Mar. 7, 2023.
Bisset, Discontinuation of thioridazine, BMJ, vol. 325, p. 967-968, Oct. 26, 2002, bmj.com. [accessed on Jun. 11, 2025].
Jacobson et al., "AXS-05 in Treatment Resistant Depression (TRD) STRIDE-1 Phase 3 Trial Topline Results", AXSOME Therapeutics, Mar. 30, 2020.
Montgomery et al., "A New Depression Scale Designed to be Sensitive to Change", British Journal of Psychiatry, vol. 134, No. 4, Apr. 1, 1979, pp. 382-389. (DOI: 10.1192/bjp.134.4.382).
Nobile et al., "Characteristics and treatment outcome of suicidal depression: Two large naturalistic cohorts of depressed outpatients", Australian and New Zealand Journal of Psychiatry, vol. 56, No. 4, pp. 347-364, 2022. (DOI: 10.1177/00048674211025697).
Jorge Lopez-Castroman et al., "Suicidal Depressed Patients Respond Less Well to Antidepressants in the Short Term", Depression and Anxiety, New York, NY, US, vol. 33, No. 6, 16 Feb. 2016, pp. 483-494. (DOI: 10.1002/DA.224 73).
Bartol et al., "Use-dependent drug-induced Brugada pattern caused by bupropion in an adolescent with depression", Journal of the American College of Cardiology, 77(18_Supplement_I), pp. 2117-2117, 2021.
International Search Report and Written Opinion, PCT/US2025/028224 mailed on Jul. 16, 2025.
SETTLE. "Tinnitus related to bupropion treatment", Psychiatry and Clinical Psychopharmacology 2014; 24: Supplement S339-S340.
Jerome, "Bupropion and drug-induced parkinsonism," The Canadian Journal of Psychiatry, 46(6), pp. 560-561, 2001.
International Search Report and Written Opinion, PCT/US2025/033094 mailed on Aug. 26, 2025.
Spravato (esketamine), Highlights of Prescribing Information, revised Jul. 2020.
Nuedexta (dextromethorphan hydrobromide and quinidine sulfate), Highlights of Prescribing Information, revised Dec. 2022.
Aplenzin (bupropion hydrobromide), Highlights of Prescribing Information, revised Mar. 2022.
Tod et al., Quantitative Prediction of Cytochrome P450 (CYP) 2D6-Mediated Drug Interactions, Clinical Pharmacokinetics, 50(8), 519-530, Aug. 2011.
Kotlyar et al., Inhibition of CYP2D6 Activity by Bupropion, Journal of Clinical Psychopharmacology, 25(2), 226-229, Jun. 2005.
Pope et al., Pharmacokinetics of Dextromethorphan after Single or Multiple Dosing in Combination with Quinidine in Extensive and Poor Metabolizers, The Journal of Clinical Pharmacology, 44(10), 1132-1142, Oct. 2004.
Auvelity (dextromethorphan hydrobromide and bupropion hydrochloride), Highlights of Prescribing Information and Medication Guide, issued Dec. 2022.
International Preliminary Report on Patentability, PCT/US2021/061492, mailed on Jun. 15, 2023.
International Search Report and Written Opinion, PCT/US2021/061492.
International Search Report and Written Opinion, PCT/US2022/012768.
International Search Report and Written Opinion, PCT/US2023/067062 mailed on Jul. 12, 2023.
Axsome Therapeutics Announces Topline Results of the Stride-1 Phase 3 Trial in Treatment Resistant Depression and Expert Call to Discuss Clinical Implications, Mar. 2020 (retrieved from internet on Jul. 19, 2023). <axsometherapeuticsinc.gcs-web.com/node/9176/pdf>.
Anderson, A.; et al. "Efficacy and Safety of AXS-05, an Oral NMDA Receptor Antagonist with Multimodal Activity, in Major Depressive Disorder: Results of a Phase 2, Double-Blind, Active-Controlled Trial" ASCP Annual Meeting 2019 (retrieved from internet on Jul. 19, 2023). <d3dyybxyjb4kyh.cloudfront.net/pdfs/SOBP+2021+AXS-05+MDD+Poster+FINAL.pdf> (May 2019).
O'Gorman, C; et al. "Rapid Effects of AXS 05, an Oral NMDA Receptor Antagonist, in Major Depressive Disorder: Results from Two Randomized, Double Blind, Controlled Trials" ASCP Annual Meeting 2021 (retrieved from internet on Jul. 19, 2023). <d3dyybxyjb4kyh.cloudfront.net/pdfs/SOBP+2021+AXS-05+MDD+Poster+FINAL.pdf> (Jun. 2021).
O'Gorman, C.; et al. "PMH40 Effects of AXS-05 on Patient Reported Depressive Symptoms in Major Depressive Disorder: Results from the GEMINI Trial" <dol.org/10.1016/j.jval.2021.04.662> (retrieved from internet on Jul. 19, 2023). Value in Health, Jun. 2021, vol. 24, Supplement 1, pp. S135.
O'Gorman, C.; et al. "P246. Rapid Antidepressant Effects and MADRS Core Symptom Improvements With AXS-05, an Oral NMDA Receptor Antagonist, in Major Depressive Disorder: Results From Two Randomized, Double-Blind. Controlled Trials" ACNP 60th Annual Meeting: Poster Abstracts P246 <nature.com/articles/s41386-021-01236-7> (retrieved from internet on Jul. 19, 2023). Neuropsychopharmacol. 46 (Suppl 1), 72-217, Dec. 2021.
International Preliminary Report on Patentability, PCT/US2022/012768, mailed on Jul. 27, 2023.
Nofziger et al., Evaluation of dextromethorphan with select antidepressant therapy for the treatment of depression in the acute care psychiatric setting, Mental Health Clinician, 9(2), 76-81, Mar. 2019.
Update: Bupropion Hydrochloride Extended-Release 300 mg Bioequivalence Studies, FDA, retrieved Mar. 2021.
FDA Draft Guidance on Bupropion Hydrochloride, revised Mar. 2013.
Forfivo XL (bupropion hydrochloride) extended-release tablets, for oral use, Highlights of Prescribing Information, revised Dec. 2019.
Forfivo XL (Bupropion HCI) extended-release tablet, NDA 22497, Jan. 25, 2010.
Wellbutrin XL (bupropion hydrochloride extended-release), Highlights of Prescribing Information, revised Mar. 2022.
Baker T. E. et al., Human Milk and Plasma Pharmacokinetics of Single-Dose Rimegepant 75mg in Healthy Lactating Women, Breastfeeding Medicine, 17(3), 277-282, 2022.
Berle J. O. et al., Antidepressant Use During Breastfeeding, Current Women's Health Reviews, 7(1), 28-34, Feb. 2011.
Briggs G. G. et al., Excretion of bupropion in breast milk, Annals of Pharmacotherapy, 27(4):431-433, Apr. 1993.
Chad L. et al., Update on antidepressant use during breastfeeding, Canadian Family Physician, 59(6), 633-634, Jun. 2013.
Chaudron L. H. et al., Bupropion and Breastfeeding: A case of a possible Infant Seizure, The Journal of clinical psychiatry, 65(6), 881-882, Jun. 2004.
Davis M. F. et al., Bupropion Levels in Breast Milk for 4 Mother-Infant Pairs: More Answers to Lingering Questions, J. Clin. Psychiatry, 70(2), 297-298, Feb. 2009.
Di Scalea T. L. et al., Antidepressant Medication Use during Breastfeeding, Clinical obstetrics and gynecology, 52 (3): 483-497, Sep. 2009.
Dwoskin L. P. et al., Review of the Pharmacology and Clinical Profile of Bupropion, and Antidepressant and Tobacco Use Cessation Agent, CNS Drug Reviews, 12(3-4), 178-207, Sep. 2006.
Gentile S, The safety of newer antidepressants in pregnancy and breastfeeding, Drug Safety, 28(2), 137-152, Feb. 2005. [doi: 10.2165/00002018-200528020-00005. PMID: 15691224.].

(56) References Cited

OTHER PUBLICATIONS

Haas J. S. et al., Bupropion in breast milk: an exposure assessment for potential treatment to prevent post-partum tobacco use, Tobacco Control, 13(1), 52-56, Mar. 2004.
Ram D. et al., Antidepressants, anxiolytics, and hypnotics in pregnancy and lactation, Indian J Psychiatry, 57(Suppl 2): S354-S371, Jul. 2015. [doi:10.4103/0019-5545.161504].
Weissman A. M. et al., Pooled Analysis of Antidepressant Levels in Lactating Mothers, Breast Milk, and Nursing Infants, Am J Psychiatry, 161(6), 1066-1078, Jun. 2004.
Horn J. R. et al., Get to Know an Enzyme: CYP206, Pharmacy Times, Jul. 2008. retrieved on Aug. 28, 2023.
International Search Report and Written Opinion, PCT/US2023/069286 mailed on Aug. 22, 2023.
International Search Report and Written Opinion, PCT/US2023/069239 mailed on Aug. 28, 2023.
International Search Report and Written Opinion, PCT/US2023/069367 mailed on Aug. 28, 2023.
International Search Report and Written Opinion, PCT/US2023/069655 mailed on Sep. 15, 2023.
International Search Report and Written Opinion, PCT/US2023/069371 mailed on Sep. 26, 2023.
International Search Report and Written Opinion, PCT/US2022/037913 mailed on Sep. 21, 2022.
Jones A et al., "Early Improvements in Functioning and Quality of Life With AXS-05 in Major Depressive Disorder: Results From the Gemini Trial ," Value in Health, Jun. 2021, vol. 24, abstract No. PHM42, p. S135. DOI:10.1016/j.jval.2021.04.662.
International Search Report and Written Opinion, PCT/US2022/074713 mailed on Sep. 21, 2022.
Axsome Therapeutics, Inc.: "MERIT: A Randomized, Double-blind, Placebo-controlled Study of AXS-05 for Relapse Prevention in Treatment Resistant Depression," ClinicalTrials.gov, NCT04608396 version 2, Mar. 24, 2021.
International Preliminary Report on Patentability, PCT/US2022/037913, issued on Jan. 18, 2024.
International Preliminary Report on Patentability, PCT/US2022/074713, issued on Feb. 22, 2024.
Chinese Pat. No. 202080004041.1 Invalidation Notice and Request issued on Jan. 15, 2024. (English translation included).
Ward K. and Citrome L.: "AXS-05: an investigational treatment for Alzheimer's disease-associated agitation", Expert Opinion on Investigational Drugs, Jul. 6, 2022, vol. 31, issue 8, pp. 773-780, DOI: 10.1080/13543784.2022.2096006.
Defendant TEVA Pharmaceuticals, Inc.'s Invalidity Contentions for U.S. Pat. Nos. 11,752,144, 11,717,518, 11,730,706 and Exhibits A-C dated Apr. 11, 2024.
International Search Report and Written Opinion, PCT/US2025/055432 mailed on Jan. 27, 2026.
International Search Report and Written Opinion, PCT/US2025/053844 mailed on Jan. 30, 2026.
International Preliminary Report on Patentability, PCT/US2024/043903, mailed on Mar. 12, 2026.
International Preliminary Report on Patentability, PCT/US2024/046359, mailed on Mar. 26, 2026.
International Search Report and Written Opinion, PCT/US2025/061679, mailed on Apr. 10, 2026.
International Search Report and Written Opinion, PCT/US2024/058092, mailed on Jan. 24, 2025.

* cited by examiner

COMPOUNDS AND COMBINATIONS THEREOF FOR TREATING NEUROLOGICAL AND PSYCHIATRIC CONDITIONS

CROSS-REFERENCE TO RELATED APPLICATIONS

This application is continuation of U.S. patent application Ser. No. 19/249,959, filed Jun. 25, 2025; which is continuation of U.S. patent application Ser. No. 18/541,574, filed Dec. 15, 2023, now U.S. Pat. No. 12,364,674; which is continuation of U.S. patent application Ser. No. 18/333,944, filed Jun. 13, 2023, now U.S. Pat. No. 11,883,373; which is continuation of U.S. patent application Ser. No. 18/158,268, filed Jan. 23, 2023, now U.S. Pat. No. 11,730,706; which claims the benefit of U.S. Provisional Pat. App. Nos. 63/359,143, filed Jul. 7, 2022, 63/370,592, filed Aug. 5, 2022, 63/396,182, filed Aug. 8, 2022, 63/373,040, filed Aug. 19, 2022, and 63/401,541, filed Aug. 26, 2022; all of which are incorporated by reference herein in their entireties.

SUMMARY

This disclosure relates to administration of a combination of: 1) about 100-110 mg, about 104-106 mg, or about 105 mg of bupropion hydrochloride, or a molar equivalent amount of a free base form or another salt form of dextromethorphan; and 2) about 40-50 mg, about 44-46 mg, or about 45 mg of dextromethorphan hydrobromide, or a molar equivalent amount of a free base form or another salt form of dextromethorphan in certain patient populations.

Some embodiments include a method of treating major depressive disorder in a patient having moderate renal impairment, comprising administering a daily dose of: (i) about 105 mg of bupropion hydrochloride and (ii) about 45 mg of dextromethorphan hydrobromide to a human patient who has moderate renal impairment and is experiencing major depressive disorder.

Some embodiments include a method of treating major depressive disorder in a patient receiving a concomitant strong CYP2D6 inhibitor, comprising administering a daily dose of: (i) about 105 mg of bupropion hydrochloride and (ii) about 45 mg of dextromethorphan hydrobromide to a human patient who has major depressive disorder and is receiving concomitant treatment with a strong CYP2D6 inhibitor.

Some embodiments include a method of treating major depressive disorder in a patient who is a known CYP2D6 poor metabolizer, comprising administering a daily dose of: (i) about 105 mg of bupropion hydrochloride and (ii) about 45 mg of dextromethorphan hydrobromide to a human patient who is experiencing major depressive disorder and is known to be a CYP2D6 poor metabolizer.

Some embodiments include a method of using an N-methyl D-aspartate (NMDA) receptor antagonist to treat major depressive disorder, comprising administering, no more than twice daily, a combination of 105 mg of bupropion hydrochloride and 45 mg of dextromethorphan hydrobromide to a human patient who is experiencing major depressive disorder, wherein the dextromethorphan acts as an uncompetitive antagonist of the NMDA receptor and a sigma-1 receptor agonist, and the human patient does not experience dissociation.

Some embodiments include a method of treating major depressive disorder in a human patient at risk of QT prolongation, comprising administering, no more than twice daily, a combination of 105 mg of bupropion hydrochloride and 45 mg of dextromethorphan hydrobromide to a human patient who is experiencing major depressive disorder and is at risk of QT prolongation and torsades de pointes, wherein electrocardiographic evaluation of QT interval is not conducted on the human patient.

Some embodiments include a method of treating agitation associated with dementia due to Alzheimer's disease in a human patient in need thereof comprising: 1) orally administering with or without food a first dosage form once daily for one week to the human patient, then administering with or without food the first dosage form twice daily to the human patient for one week; and 2) then orally administering with or without food a second dosage form twice daily to the human patient thereafter, for a total of at least five week; wherein the human patient is not a CYP2D6 poor metabolizer, and does not have moderate renal impairment; wherein the first and second dosage forms are bilayer tablets; wherein the first dosage form comprises about 30 mg of dextromethorphan hydrobromide, or a molar equivalent amount of another salt form of dextromethorphan or the free base form of dextromethorphan, about 105 mg of bupropion hydrochloride, or a molar equivalent amount of another salt form of bupropion or the free base form of bupropion, and a polymer; and wherein the second dosage form comprises about 45 mg of dextromethorphan hydrobromide, or a molar equivalent amount of another salt form of dextromethorphan or the free base form of dextromethorphan, and about 105 mg of bupropion hydrochloride, or a molar equivalent amount of another salt form of bupropion or the free base form of bupropion.

DETAILED DESCRIPTION

Figure 1:
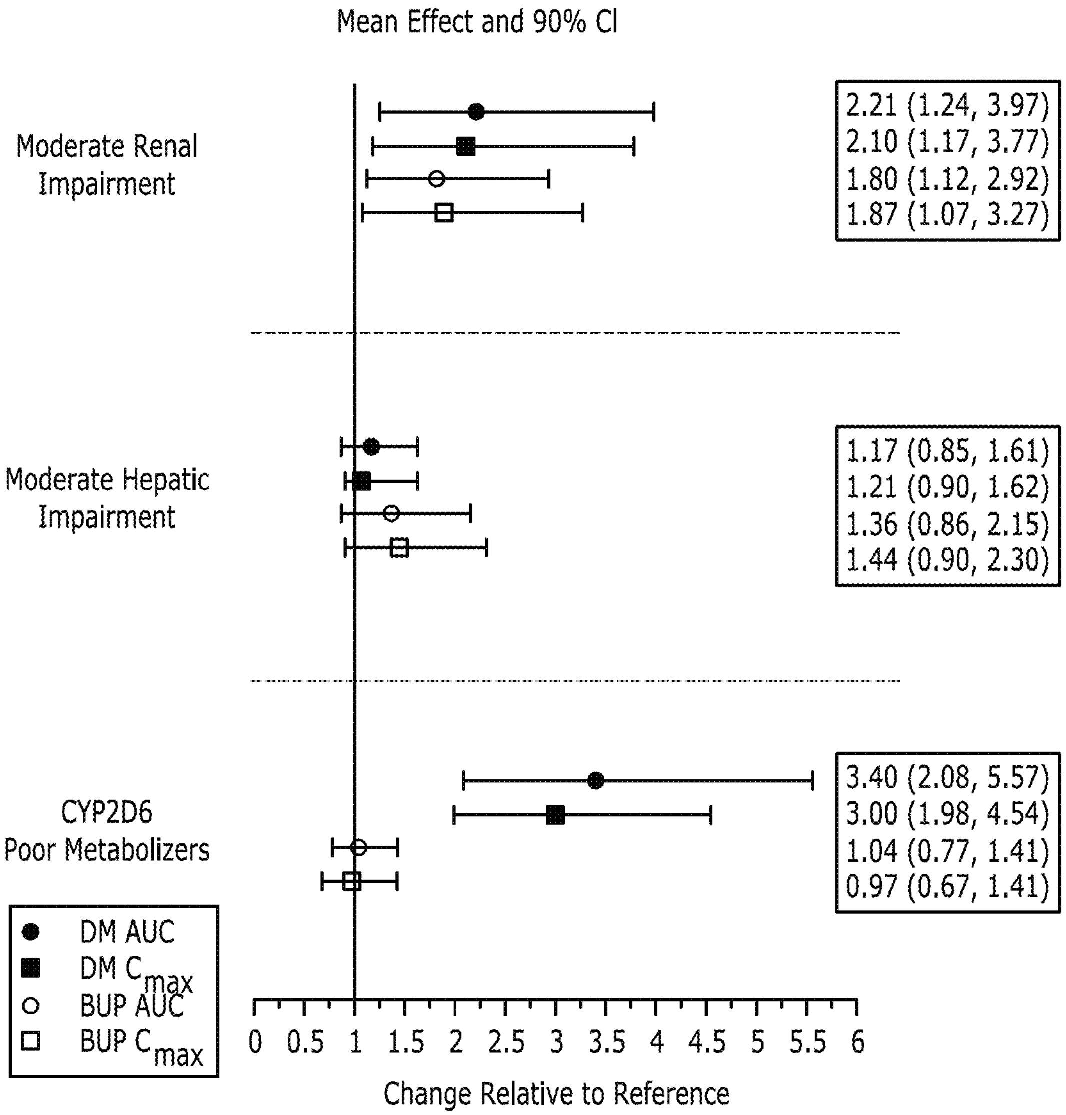
FIG. 1 depicts the effects of renal impairment, hepatic impairment, and CYP2D6 poor metabolizer status on the pharmacokinetics of a tablet containing 45 mg of dextromethorphan hydrobromide and 105 mg of bupropion hydrochloride.

As mentioned above, this disclosure relates to administration of a combination of: 1) about 100-110 mg, about 104-106 mg, or about 105 mg of bupropion hydrochloride, or a molar equivalent amount of a free base form or another salt form of dextromethorphan; and 2) about 40-50 mg, about 44-46 mg, or about 45 mg of dextromethorphan hydrobromide, or a molar equivalent amount of a free base form or another salt form of dextromethorphan. This combination is referred to for convenience herein as the "subject combination." In every instance where the subject combination is referred to herein, the combination of 105 mg of bupropion hydrochloride and 45 mg of dextromethorphan hydrobromide is specifically contemplated.

Dextromethorphan hydrobromide is an uncompetitive NMDA receptor antagonist and A sigma-1 receptor agonist. The chemical name of dextromethorphan hydrobromide is morphinan, 3-methoxy-17-methyl-, (9α, 13α, 14α), hydrobromide monohydrate. Dextromethorphan hydrobromide has the empirical formula $C_{18}H_{25}NO \cdot HBr \cdot H_2O$ and a molecular weight of 370.33. The structural formula is:

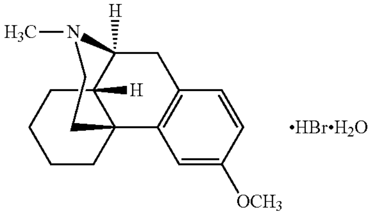

Dextromethorphan hydrobromide powder is white or almost white, crystalline, and sparingly soluble in water.

Bupropion hydrochloride is an aminoketone and CYP450 2D6 inhibitor.

The chemical name of bupropion hydrochloride is: (±)-1-(3-chlorophenyl)-2-[(1,1-dimethylethyl)amino]-1-propanone hydrochloride. Bupropion hydrochloride has the empirical formula $C_{13}H_{18}ClNO \cdot HCl$ and a molecular weight of 276.2. The structural formula is:

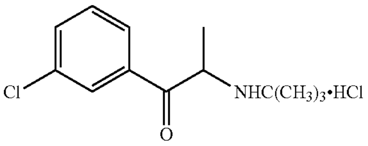

Bupropion hydrochloride powder is white and highly soluble in water.

The subject combination may be contained in an oral dosage form, including a tablet, such as an extended-release tablet. In some embodiments, the subject combination is contained in a dosage form for oral administration and is available as round bilayer tablets.

In some embodiments, each tablet containing the subject combination contains 45 mg of dextromethorphan hydrobromide in an immediate-release formulation. In some embodiments, each tablet of the subject combination contains 105 mg of bupropion hydrochloride in an extended-release formulation. In some embodiments, each tablet of the subject combination contains 45 mg of dextromethorphan hydrobromide in an immediate-release formulation and 105 mg of bupropion hydrochloride in an extended-release formulation.

In some embodiments, a tablet containing the subject combination contains 1-cysteine hydrochloride monohydrate. In some embodiments, a tablet containing the subject combination contains carbomer homopolymer. In some embodiments, a tablet containing the subject combination contains microcrystalline cellulose. In some embodiments, a tablet containing the subject combination contains colloidal silicon dioxide. In some embodiments, a tablet containing the subject combination contains crospovidone. In some embodiments, a tablet containing the subject combination contains stearic acid. In some embodiments, a tablet containing the subject combination contains magnesium stearate.

In some embodiments, a tablet containing the subject combination contains the following inactive ingredients: 1-cysteine hydrochloride monohydrate, carbomer homopolymer, microcrystalline cellulose, colloidal silicon dioxide, crospovidone, stearic acid, and magnesium stearate.

In some embodiments, the starting dosage of the subject combination is 45 mg of dextromethorphan hydrobromide and 105 mg of bupropion hydrochloride in one tablet that is administered once daily in the morning. In some embodiments, after 3 days, the dosage is increased to one tablet (or one dosage form containing 45 mg of dextromethorphan hydrobromide and 105 mg of bupropion hydrochloride) twice daily, e.g., given at least 8 hours apart. In some embodiments, no more than two doses containing 45 mg of dextromethorphan hydrobromide and 105 mg of bupropion hydrochloride are administered in the same day.

The subject combination may be administered orally with or without food. In some embodiments, the tablets are swallowed whole, and not crushed, divided, or chewed.

Patients having renal impairment may require special dosing. In some embodiments, the recommended dosage of the subject combination for patients with moderate renal impairment (estimated glomerular filtration rate (eGFR) or glomerular filtration rate (GFR) of 30 to 59 mL/minute/1.73 $m^2$) is a daily dose of 45 mg of dextromethorphan hydrobromide and 105 mg of bupropion hydrochloride, or a molar equivalent amount of another form of dextromethorphan and/or bupropion, such as administration of one tablet (or one dosage form containing 45 mg of dextromethorphan hydrobromide and 105 mg of bupropion hydrochloride) once daily, such as one tablet or other oral dosage form daily in the morning.

Patients who are concomitantly using the subject combination with strong CYP2D6 inhibitors may require special dosing. Concomitant use of the subject combination with a strong CYP2D6 inhibitor increases plasma concentrations of dextromethorphan. In some embodiments, the recommended dosage of the subject combination when coadministered with a strong CYP2D6 inhibitor is one tablet (or one dosage form containing 45 mg of dextromethorphan hydrobromide and 105 mg of bupropion hydrochloride) once daily, such as one tablet or other oral dosage form daily in the morning. In some embodiments, the patients are monitored for adverse reactions potentially attributable to dextromethorphan, such as somnolence and dizziness.

Patients who are known CYP2D6 poor metabolizers (PMs) may require special dosing. In some embodiments, the recommended dosage for patients known to be poor CYP2D6 metabolizers is one tablet (or one dosage form containing 45 mg of dextromethorphan hydrobromide and 105 mg of bupropion hydrochloride) once daily, such as one tablet or other oral dosage form daily in the morning.

Special precautions may be required when switching a patient to or from a monoamine oxidase inhibitor (MAOI) antidepressant to the subject combination. In some embodiments, at least 14 days must elapse between discontinuation of an MAOI intended to treat depression and initiation of therapy with the subject combination. Conversely, in some embodiments, at least 14 days must be allowed after stopping the subject combination before starting an MAOI antidepressant.

In the subject combination, bupropion inhibits the metabolism of dextromethorphan via CYP2D6. Dextromethorphan, when co-administered with bupropion, displays nonlinear pharmacokinetics at steady state, with greater than dose-proportional changes in AUC and $C_{max}$ for varying doses of dextromethorphan (30 to 60 mg) and less than dose-proportional changes for varying doses of bupropion (75 to 150 mg).

Steady state plasma concentrations of dextromethorphan and bupropion when given as the subject combination are achieved within 8 days. The accumulation ratios for dextromethorphan at steady state are about 20 and about 32, respectively based on $C_{max}$ and $AUC_{0-12}$. The accumulation ratios for bupropion at steady state are 1.1 and 1.5, respectively based on $C_{max}$ and $AUC_{0-12}$.

After administration of the subject combination, the median $T_{max}$ of dextromethorphan is about 3 hours and the median $T_{max}$ of bupropion is about 2 hours. The $C_{max}$ of hydroxybupropion metabolite occurs approximately 3 hours post-dose and is approximately 14 times the peak level of bupropion. The $AUC_{0-12}$ hydroxybupropion is about 19 times that of bupropion. The $C_{max}$ of the erythrohydroxybupropion and threohydroxybupropion metabolites occurs approximately 4 hours post-dose and is approximately equal to and about 5 times that of bupropion, respectively. The $AUC_{0-12}$ values of erythrohydroxybupropion and threohydroxybupropion are about 1.2 and about 7 times that of bupropion, respectively.

The subject combination can be taken with or without food. Dextromethorphan $C_{max}$ and $AUC_{0-12}$ were unchanged and decreased by 14%, respectively, and bupropion $C_{max}$ and $AUC_{0-12}$ were increased by 3% and 6%, respectively, when the subject combination was administered with food.

The plasma protein binding of dextromethorphan is approximately 60-70% and bupropion is 84%. The extent of protein binding of the hydroxybupropion metabolite is similar to that for bupropion; whereas the extent of protein binding of the threohydroxybupropion metabolite is about half that seen with bupropion.

Following 8 days of administration of the subject combination in extensive metabolizers, the mean elimination half-life of dextromethorphan was increased approximately 3-fold to about 22 hours, as compared to dextromethorphan given without bupropion.

The mean elimination half-life of dextromethorphan and bupropion was 22 hours and 15 hours, respectively. The apparent elimination half-life of hydroxybupropion, erythrohydroxybupropion and threohydroxybupropion metabolites were approximately 35, 44 and 33 hours, respectively.

Esketamine is a non-competitive NMDA receptor antagonist indicated, in conjunction with an oral antidepressant, for the treatment of treatment-resistant depression in adults. Treatment of treatment-resistant depression carries a risk of dissociation. The label for esketamine states that because of the risks of sedation and dissociation, patients must be monitored for at least 2 hours at each treatment session, followed by an assessment to determine when the patient is considered clinically stable and ready to leave the healthcare setting.

Dissociation includes: delusional perception; depersonalization/derealization disorder; derealization; diplopia; dissociation; dysesthesia; feeling cold; feeling hot; feeling of body temperature change; hallucination; hallucination, auditory; hallucination, visual; hyperacusis; illusion; ocular discomfort; oral dysesthesia; paranesthesia; paranesthesia oral; pharyngeal paranesthesia; photophobia; time perception altered; tinnitus; vision blurred; visual impairment.

The subject combination is a combination of dextromethorphan, an uncompetitive N-methyl D-aspartate (NDMA) receptor antagonist and sigma-1 receptor agonist, and bupropion, an aminoketone and CYP450 2D6 inhibitor, indicated for the treatment of major depressive disorder (MDD) in adults. Unlike esketamine, the subject combination can be administered as a without dissociation or dissociative events. In some embodiments, the patient is not monitored for dissociation after the subject combination is administered.

Unlike the combination of quinidine and dextromethorphan, at a dose of a combination of 105 mg of bupropion hydrochloride and 45 mg of dextromethorphan hydrobromide given twice a day, the subject combination does not prolong the QT interval to any clinically relevant extent. Thus, for a human patient who is experiencing major depressive disorder and is at risk of QT prolongation and torsades de pointes, electrocardiographic evaluation of QT interval is not typically conducted on the human patient.

The subject combination may be used for adjunctive treatment of major depressive disorder or depression.

In addition to major depressive disorder, the subject combination may be used to treat other diseases in conditions in the patient populations or circumstances described herein. For example, the subject combination may be used to treat pain or a neurological disorder. Examples of neurological disorders that may be treated with the subject combination include, but are not limited to: affective disorders, psychiatric disorders, cerebral function disorders, movement disorders, dementias, motor neuron diseases, neurodegenerative diseases, seizure disorders, and headaches.

Affective disorders that may be treated by the subject combination include, but are not limited to, depression, major depression, treatment resistant depression, treatment resistant bipolar depression, bipolar disorders including cyclothymia, seasonal affective disorder, mood disorders, chronic depression (dysthymia), psychotic depression, postpartum depression, premenstrual dysphoric disorder (PMDD), situational depression, atypical depression, mania, anxiety disorders, attention deficit disorder (ADD), attention deficit disorder with hyperactivity (ADDH), and attention deficit/hyperactivity disorder (AD/HD), bipolar and manic conditions, obsessive-compulsive disorder, bulimia, obesity or weight-gain, narcolepsy, chronic fatigue syndrome, premenstrual syndrome, substance addiction or abuse, nicotine addiction, psycho-sexual dysfunction, pseudobulbar affect, and emotional lability.

Depression may be manifested by depressive symptoms. These symptoms may include psychological changes such as changes in mood, feelings of intense sadness, despair, mental slowing, loss of concentration, pessimistic worry, agitation, anxiety, irritability, guilt, anger, feelings of worthlessness, reckless behavior, suicidal thoughts, or attempts, and/or self-deprecation. Physical symptoms of depression may include insomnia, anorexia, appetite loss, weight loss, weight gain, decreased energy and libido, fatigue, restlessness, aches, pains, headaches, cramps, digestive issues, and/or abnormal hormonal circadian rhythms.

Psychiatric disorders that may be treated by the subject combination, include, but are not limited to, anxiety disorders, including but not limited to, phobias, generalized anxiety disorder, social anxiety disorder, panic disorder, agoraphobia, obsessive-compulsive disorder, and post-traumatic stress disorder (PTSD); mania, manic depressive illness, hypomania, unipolar depression, depression, stress disorders, somatoform disorders, personality disorders, psychosis, schizophrenia, delusional disorder, schizoaffective disorder, schizotypy, aggression, aggression in Alzheimer's disease, agitation, and agitation in Alzheimer's disease. Alzheimer's disease may also be referred to as dementia of the Alzheimer's type. Other neurobehavioral symptoms of Alzheimer's disease that may be treated include disinhibition and apathy.

Agitation in Alzheimer's disease occurs as the disease progresses. Agitation may present itself as inappropriate verbal, emotional, and/or physical behaviors. Inappropriate behaviors may include, but are not limited to, incoherent babbling, inappropriate emotional response, demands for attention, threats, irritability, frustration, screaming, repetitive questions, mood swings, cursing, abusive language, physical outbursts, emotional distress, restlessness, shredding, sleeping disturbances, delusions, hallucinations, pacing, wandering, searching, rummaging, repetitive body motions, hoarding, shadowing, hitting, scratching, biting, combativeness, hyperactivity, and/or kicking.

Alzheimer's disease (AD) is a progressive neurodegenerative disorder characterized by cognitive decline, and behavioral and psychological symptoms including agitation. AD is the most common form of dementia and afflicts an estimated 6 million individuals in the United States, a number that is anticipated to increase to approximately 14 million by 2050. Agitation is reported in up to 70% of patients with AD and is characterized by emotional distress, aggressive behaviors, disruptive irritability, and disinhibition. Managing agitation is a priority in AD. Agitation in patients with AD has been associated with increased caregiver burden, decreased functioning, accelerated cognitive decline, earlier nursing home placement, and increased mortality. There are currently no therapies approved by the FDA for the treatment of agitation in patients with AD.

Neurobehavioral symptoms have been known to appear during dementia and may be treated by the combination. Caregivers or families may feel more overwhelmed by patients' behavioral/psychological symptoms than by their cognitive impairment. Common forms of the syndrome are Alzheimer's disease, vascular dementia, dementia with Lewy bodies (abnormal aggregates of protein that develop inside nerve cells), and a group of diseases that contribute to frontotemporal dementia (degeneration of the frontal lobe of the brain). The symptoms that dementia patients have are similar to those of psychiatric disorders, but some are slightly different from each other. Neurobehavioral symptoms associated with dementia include depression, apathy, agitation, disinhibition, hallucinations, delusions, psychosis, impulsiveness, aggressiveness, compulsion, excessive sex drive, and personality disorders. Neurobehavioral symptoms such as disinhibition may also be found in other conditions such as traumatic brain injury.

Agitation in patients with Alzheimer's disease may be assessed using the Cohen Mansfield Agitation Inventory or CMAI. The CMAI assesses various behaviors including, Hitting (including self), Kicking, Grabbing onto people, Pushing, Throwing things, Biting, Scratching, Spitting, Hurting self or others, Tearing things or destroying property, Making physical sexual advances, Pacing, aimless wandering, Inappropriate dress or disrobing, Trying to get to a different place, Intentional falling, Eating/drinking inappropriate substances, Handling things inappropriately, Hiding things, Hoarding things, Performing repetitive mannerisms, General restlessness, Screaming, Making verbal sexual advances, Cursing or verbal aggression, Repetitive sentences or questions, Strange noises (weird laughter or crying), Complaining, Negativism, Constant unwarranted request for attention or help.

Schizophrenia may be treated by the combination including positive symptoms and/or negative symptoms of schizophrenia, or residual symptoms of schizophrenia. Other conditions that may treated include intermittent explosive disorder.

Cerebral function disorders that may be treated by the subject combination include, but are not limited to, disorders involving intellectual deficits such as senile dementia, Alzheimer's type dementia, memory loss, amnesia/amnestic syndrome, epilepsy, disturbances of consciousness, coma, lowering of attention, speech disorders, voice spasms, Parkinson's disease, Lennox-Gastaut syndrome, autism, hyperkinetic syndrome, and schizophrenia. Cerebral function disorders also include disorders caused by cerebrovascular diseases including, but not limited to, stroke, cerebral infarction, cerebral bleeding, cerebral arteriosclerosis, cerebral venous thrombosis, head injuries, and the like where symptoms include disturbance of consciousness, senile dementia, coma, lowering of attention, and speech disorders.

Substance addiction abuse that may be treated by the subject combination includes, but is not limited to, drug dependence, addiction to cocaine, psychostimulants (e.g., crack, cocaine, speed, meth), nicotine, alcohol, opioids, anxiolytic and hypnotic drugs, cannabis (marijuana), amphetamines, hallucinogens, phencyclidine, volatile solvents, and volatile nitrites. Nicotine addiction includes nicotine addiction of all known forms, such as smoking cigarettes, cigars and/or pipes, e-cigarettes or vaping, and addiction to chewing tobacco.

Movement disorders that may be treated by the subject combination include, but are not limited to, akathisia, akinesia, associated movements, athetosis, ataxia, ballismus, hemiballismus, bradykinesia, cerebral palsy, chorea, Huntington's disease, Huntington's disease chorea, rheumatic chorea, Sydenham's chorea, dyskinesia, tardive dyskinesia, dystonia, blepharospasm, spasmodic torticollis, dopamine-responsive dystonia, Parkinson's disease, restless legs syndrome (RLS), tremor, essential tremor, and Tourette's syndrome, and Wilson's disease.

Dementias that may be treated by the subject combination include, but are not limited to, Alzheimer's disease, Parkinson's disease, vascular dementia, dementia with Lewy bodies, mixed dementia, fronto-temporal dementia, Creutzfeldt-Jakob disease, normal pressure hydrocephalus, Huntington's disease, Wernicke-Korsakoff Syndrome, and Pick's disease.

Motor neuron diseases that may be treated by the subject combination include, but are not limited to, amyotrophic lateral sclerosis (ALS), progressive bulbar palsy, primary lateral sclerosis (PLS), progressive muscular atrophy, post-polio syndrome (PPS), spinal muscular atrophy (SMA), spinal motor atrophies, Tay-Sach's disease, Sandhoff disease, and hereditary spastic paraplegia.

Neurodegenerative diseases that may be treated the subject combination include, but are not limited to, Alzheimer's disease, prion-related diseases, cerebellar ataxia, spinocerebellar ataxia (SCA), spinal muscular atrophy (SMA), bulbar muscular atrophy, Friedrich's ataxia, Huntington's disease, Lewy body disease, Parkinson's disease, amyotrophic lateral sclerosis (ALS or Lou Gehrig's disease), multiple sclerosis (MS), multiple system atrophy, Shy-Drager syndrome, corticobasal degeneration, progressive supranuclear palsy, Wilson's disease, Menkes disease, adrenoleukodystrophy, cerebral autosomal dominant arteriopathy with subcortical infarcts and leukoencephalopathy (CADASIL), muscular dystrophies, Charcot-Marie-Tooth disease (CMT), familial spastic paraparesis, neurofibromatosis, olivopontine cerebellar atrophy or degeneration, striatonigral degeneration, Guillain-Barre syndrome, and spastic paraplesia.

Seizure disorders that may be treated by the subject combination include, but are not limited to, epileptic seizures, nonepileptic seizures, epilepsy, febrile seizures; partial seizures including, but not limited to, simple partial seizures, Jacksonian seizures, complex partial seizures, and epilepsia partialis continua; generalized seizures including, but not limited to, generalized tonic-clonic seizures, absence seizures, atonic seizures, myoclonic seizures, juvenile myoclonic seizures, and infantile spasms; and status epilepticus.

Types of headaches that may be treated by the subject combination include, but are not limited to, migraine, tension, and cluster headaches.

Other neurological disorders that may be treated by the subject combination include, Rett Syndrome, autism, tinnitus, disturbances of consciousness disorders, sexual dysfunction, intractable coughing, narcolepsy, cataplexy; voice disorders due to uncontrolled laryngeal muscle spasms, including, but not limited to, abductor spasmodic dysphonia, adductor spasmodic dysphonia, muscular tension dysphonia, and vocal tremor; diabetic neuropathy, chemotherapy-induced neurotoxicity, such as methotrexate neurotoxicity; incontinence including, but not limited, stress urinary incontinence, urge urinary incontinence, and fecal incontinence; and erectile dysfunction.

In some embodiments, the subject combination may be used to treat pain, joint pain, pain associated with sickle cell disease, pseudobulbar affect, depression (including treatment resistant depression), disorders related to memory and cognition, schizophrenia, Parkinson's disease, amyotrophic lateral sclerosis (ALS), Rhett's syndrome, seizures, cough (including chronic cough), etc.

In some embodiments, the subject combination may be administered orally to relieve musculoskeletal pain including low back pain, and pain associated with rheumatoid arthritis, juvenile rheumatoid arthritis, osteoarthritis, erosive osteoarthritis, sero-negative (non-rheumatoid) arthropathies, non-articular rheumatism, peri-articular disorders, axial spondyloarthritis including ankylosing spondylitis, Paget's disease, fibrous dysplasia, SAPHO syndrome, transient osteoarthritis of the hip, vertebral crush fractures, osteoporosis, etc.

In some embodiments, the subject combination may be administered to relieve inflammatory pain including musculoskeletal pain, arthritis pain, and complex regional pain syndrome.

Arthritis refers to inflammatory joint diseases that can be associated with pain. Examples of arthritis pain include pain associated with osteoarthritis, erosive osteoarthritis, rheumatoid arthritis, juvenile rheumatoid arthritis, sero-negative (non-rheumatoid) arthropathies, non-articular rheumatism, peri-articular disorders, neuropathic arthropathies including Charcot's foot, axial spondyloarthritis including ankylosing spondylitis, and SAPHO syndrome.

In some embodiments, the subject combination is used to treat chronic musculoskeletal pain.

In some embodiments, the subject composition may be administered to relieve complex regional pain syndrome, such as complex regional pain syndrome type I (CRPS-I), complex regional pain syndrome type II (CRPS-II), CRPS-NOS, or another type of CRPS. CRPS is a type of inflammatory pain. CRPS can also have a neuropathic component. Complex regional pain syndrome is a debilitating pain syndrome. It is characterized by severe pain in a limb that can be accompanied by edema, and autonomic, motor, and sensory changes.

In some embodiments, the subject composition may be administered orally to relieve neuropathic pain.

Examples of neuropathic pain include pain due to diabetic peripheral neuropathy or diabetic peripheral neuropathic pain, post-herpetic neuralgia, trigeminal neuralgia, monoradiculopathies, phantom limb pain, central pain, pain due to multiple sclerosis, etc. Other causes of neuropathic pain include cancer-related pain, lumbar nerve root compression, spinal cord injury, post-stroke pain, central multiple sclerosis pain, HIV-associated neuropathy, and radio- or chemotherapy associated neuropathy, etc.

In some embodiments, the subject composition may be administered to relieve fibromyalgia.

The term "treating" or "treatment" includes the diagnosis, cure, mitigation, treatment, or prevention of disease in man or other animals, or any activity that otherwise affects the structure or any function of the body of man or other animals.

A subject combination may be used to treat any disease or condition identified as treatable by the combination of bupropion and dextromethorphan in any of the following U.S. Pat. Nos. 8,569,328, 9,168,234, 9,189,905 9,205,083, 9,238,032, 9,278,095, 9,314,462, 9,370,513, 9,375,429, 9,408,815, 9,421,176, 9,457,023, 9,457,025, 9,474,731, 9,486,450, 9,700,528, 9,700,553, 9,707,191, 9,763,932, 9,861,595, 9,867,819, 9,968,568, 10,058,518, 10,064,857, 10,080,727, 10,092,560, 10,092,561, 10,105,327, 10,105,361, 10,251,879, 10,463,634, 10,512,643, 10,548,857, 10,596,167, 10,772,850, 10,780,064, 10,780,066, 10,786,469, 10,786,496, 10,799,497, 10,806,710, 10,864,209, 10,874,663, 10,874,664, 10,874,665, 10,881,624, 10,881,657, 10,894,046, 10,894,047, 10,898,453, all of which are incorporated by reference herein in their entireties for their disclosure of diseases that may be treated by a combination of bupropion and dextromethorphan, including specific embodiments and combinations described therein.

Example 1

In a study of the subject combination in 7 subjects with moderate (GFR 30-60 mL/min) renal impairment compared to 6 matched controls with normal renal function (matched in gender, age, and weight range to impaired subjects), both dextromethorphan and bupropion exposures increased by approximately 2-fold and clearances were reduced by 50%.

Example 2

Approximately 7 to 10% of Caucasians and 3 to 8% of African Americans lack the capacity to metabolize CYP2D6 substrates and are classified as poor metabolizers. In 3 poor metabolizers the pharmacokinetics of the subject combination resulted in an approximate 3-fold and 3.4-fold increase in dextromethorphan $C_{max}$ and $AUC_{0-12}$, respectively, compared to extensive metabolizers. An exploration of steady state pharmacokinetic data in 12 poor metabolizers treated with the subject combination in efficacy trials showed plasma concentrations of dextromethorphan that were generally higher than exposures for non-poor metabolizers.

Example 3

Co-administration of the SSRI paroxetine and the subject combination was studied in 29 healthy volunteers. Paroxetine increased the overall exposure of dextromethorphan by 2.5-fold and had no effect on bupropion. The overall exposure of paroxetine was increased by 1.2-fold when co-administered with the subject combination. Based on these results, when the subject combination is prescribed with drugs that inhibit CYP2D6, the subject combination should be dosed once daily. Use caution when administering the subject combination in conjunction with drugs which are extensively metabolized via CYP2D6.

Example 4

The properties of a tablet containing a combination of dextromethorphan hydrobromide, which is an uncompetitive NMDA receptor antagonist and sigma-1 receptor agonist, and bupropion hydrochloride, which is an aminoketone and CYP450 2D6 inhibitor, were studied.

The tablets are for oral administration and are round bilayer tablets. Each tablet contains 45 mg dextromethorphan hydrobromide (equivalent to 32.98 mg of the dextromethorphan free base) in an immediate-release formulation and 105 mg bupropion hydrochloride (equivalent to 91.14 mg of the bupropion free base) in an extended-release formulation. Each tablet contains the following inactive ingredients: carbomer homopolymer, colloidal silicon dioxide, crospovidone, glyceryl monocaprylocaprate, 1-cysteine hydrochloride monohydrate, magnesium stearate, microcrystalline cellulose, polyvinyl alcohol, red iron oxide, sodium lauryl sulfate, stearic acid, talc, titanium dioxide, and/or yellow iron oxide.

The effects of renal impairment, hepatic impairment, and CYP2D6 poor metabolizer status on the exposure to a tablet containing 45 mg of dextromethorphan hydrobromide and 105 mg of bupropion hydrochloride are summarized in FIG. 1.

Results depicted in FIG. 1 are based on plasma concentrations in human patients after 8 days of twice daily dosing of a tablet containing 45 mg of dextromethorphan hydrobromide and 105 mg of bupropion hydrochloride. Data are GMRs and 90% CIs. Reference used are the matched healthy subjects for renal and hepatic impairment studies, and extensive or ultra-extensive CYP2D6 metabolizers. AUC represents the area under the plasma concentration-time curve from zero to 12 hours; BUP represents bupropion; Cl is confidence interval; $C_{max}$ is maximum plasma concentration; DM represents dextromethorphan; GMRs represents geometric mean ratios; PK represents pharmacokinetics.

For patients having moderate renal impairment, a 2.21-fold increase in dextromethorphan $AUC_{0-12}$, a 2.10-fold increase in dextromethorphan $C_{max}$, a 1.80-fold increase in bupropion $AUC_{0-12}$, and a 1.87-fold increase in bupropion $C_{max}$ were observed.

Based upon these results, dosage adjustment is recommended in patients known to have moderate renal impairment because these patients have higher dextromethorphan and bupropion concentrations than patients with healthy renal function. The recommended total daily dose for patients known to have moderate renal impairment is about 45 mg of dextromethorphan hydrobromide and about 105 mg of bupropion hydrochloride (e.g. one tablet containing about 45 mg of dextromethorphan hydrobromide and about 105 mg of bupropion hydrochloride for administration once daily, such as in the morning), or an equivalent dose of another form dextromethorphan and/or bupropion.

Example 5

A Phase 2/3 randomized, double-blind, controlled, multicenter, U.S. clinical trial was conducted to evaluate the efficacy and safety of DM/BU in patients with agitation associated with Alzheimer's disease. A total of 366 patients with a diagnosis of probable Alzheimer's disease and clinically meaningful agitation associated with their disease were randomized, initially in a 1:1:1 ratio, to receive DM/BU (dextromethorphan/bupropion, dose escalated from 30 mg/105 mg once daily in the first week, to 30 mg/105 mg twice daily in the second week, to 45 mg/105 mg twice daily thereafter), bupropion (dose escalated from 105 mg once daily in the first week to 105 mg twice daily thereafter), or matching placebo, for 5 weeks. An independent data monitoring committee performed an interim futility analysis and recommended no further randomization to the bupropion arm. Subsequently, patients were randomized in a 1:1 ratio to receive DM/BU or placebo. Total patients randomized were 159, 49, and 158 to the DM/BU, bupropion, and placebo arms, respectively. The mean Cohen-Mansfield Agitation Inventory (CMAI) total scores at baseline were 60.8, 66.1, and 59.3, respectively for the DM/BU, bupropion, and placebo groups. The minimum score on the CMAI is 29, corresponding to the total absence of symptoms, with higher scores corresponding to greater agitation. The primary endpoint of the study was the change from baseline in the CMAI total score at Week 5. P-values were calculated based on least square mean estimates.

Inclusion criteria included male or female 65-90 years of age, diagnosis of probable Alzheimer's disease, according to the 2011 NIA-AA criteria, diagnosis of agitation, according to the IPA provisional definition of agitation, MMSE score between 10 and 24, an NPI-AA score≥4, and community dwelling. Exclusion criterial included dementia of non-Alzheimer's type and current use of a selective serotonin reuptake inhibitor and/or a serotonin and norepinephrine inhibitor (SSRI/SNRI). Demographics and baseline characteristics are shown in Table 1 below.

TABLE 1

Demographics and Baseline Characteristics

| | DM/BU (n = 152) | Bupropion (n = 49) | Placebo (n = 156) |
|---|---|---|---|
| Age (years) | 75.2 (5.71) | 76.4 (6.13) | 75.1 (5.96) |
| Female Gender, n (%) | 86 (56.6%) | 22 (44.9%) | 91 (58.3%) |
| Race, n (%) | | | |
| White | 136 (89.5%) | 43 (87.8%) | 128 (82.1%) |
| Black or African American | 11 (7.2%) | 5 (10.2%) | 25 (16.0%) |
| Asian | 1 (0.7%) | 0 | 1 (0.6%) |
| Other or Not Reported | 4 (2.6%) | 1 (2.0%) | 2 (1.3%) |
| CMAI Score | 60.7 (17.40) | 66.1 (19.65) | 59.4 (15.60) |
| CGI-S (agitation) | 4.2 (0.77) | 4.4 (0.82) | 4.2 (0.65) |
| NPI-A/A Score | 7.2 (2.17) | 6.9 (2.45) | 6.8 (2.07) |
| MMSE | 18.7 (3.76) | 17.8 (4.19) | 18.8 (3.70) |

mITT population. Data are mean (SD) unless otherwise stated.
Abbreviations: BMI = Body Mass Index;
BU = bupropion;
CGI-S = Clinical Global Impression - Severity;
CMAI = Cohen-Mansfield Agitation Inventory;
DM = dextromethorphan;
mITT = modified intent to treat;
MMSE = Mini-mental state examination;
NPI-A/A = Neuropsychiatric
Inventory - Agitation and Aggressive domain.

Figure 2:
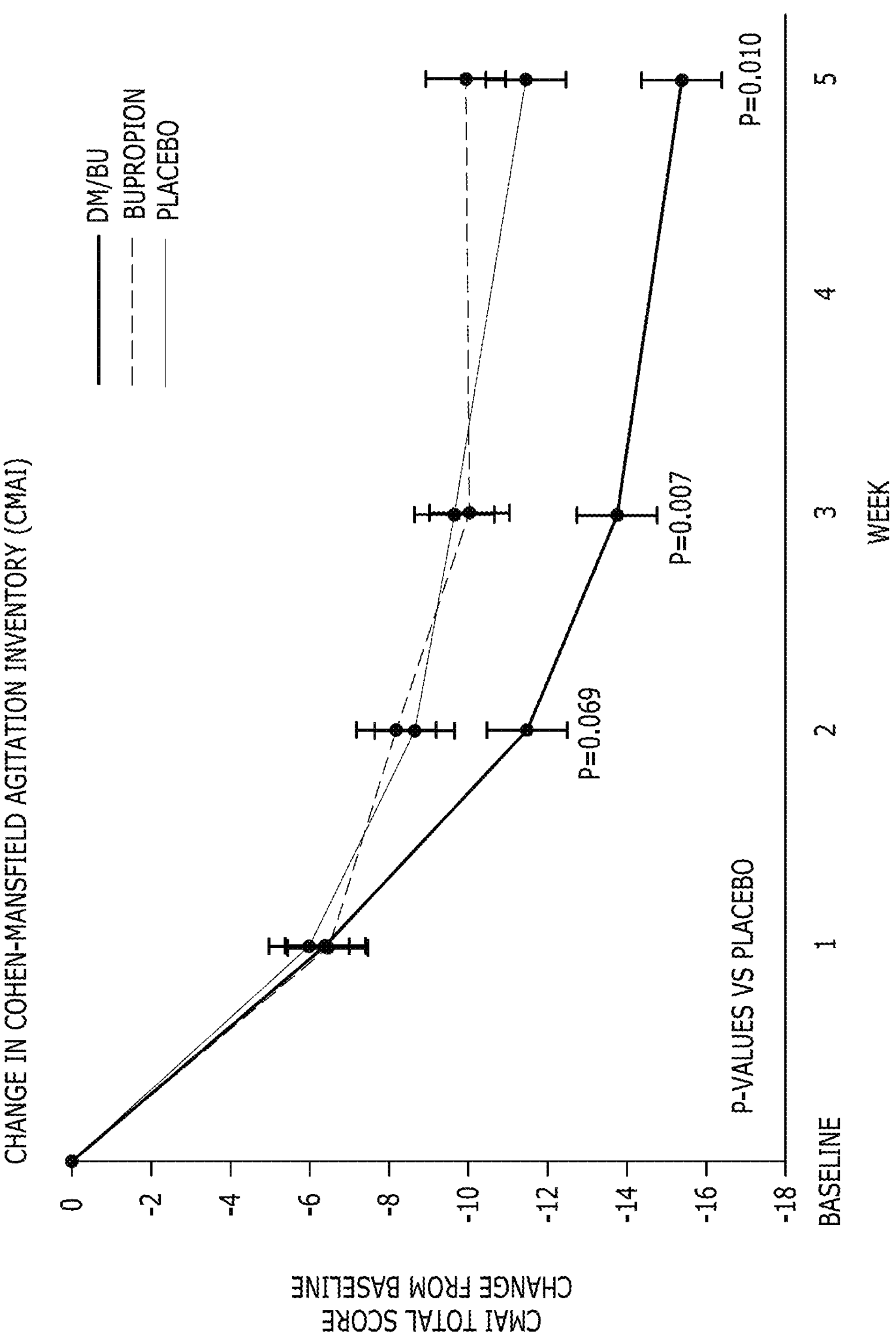
FIG. 2 is a plot of the CMAI total score change from baseline over time for the subjects described in Example 5.

As shown in FIG. 2, DM/BU met the primary endpoint by demonstrating a statistically significant mean reduction in the Cohen Mansfield Agitation Inventory (CMAI) total score compared to placebo at Week 5, with mean reductions from baseline of 15.4 points for DM/BU (n=152), 10.0 for BU 9n=49), and 11.5 points for placebo (n=156) (p=0.010).

Figure 3:
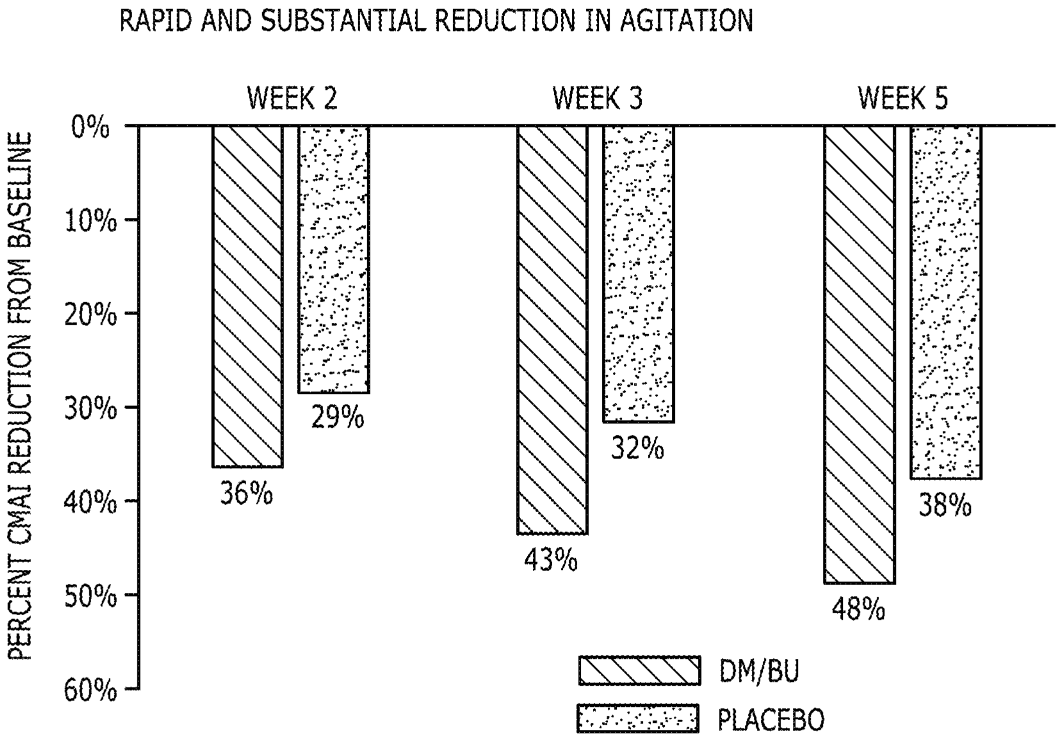
FIG. 3 is a plot of the percent CMAI reduction from baseline over time for the subjects described in Example 5.

As shown in FIG. 3, These results represent a mean percentage reduction of CMAI from baseline of 48% for DM/BU versus 38% for placebo. The CMAI is a 29-item caregiver-rated scale that assesses the frequency of agitation-related behaviors in patients with dementia, including excessive motor activity such as pacing and restlessness, verbal aggression such as screaming and shouting, and physical aggression such as grabbing, pushing, and hitting. DM/BU was also statistically superior to bupropion on the CMAI total score (p<0.001) at week 5, demonstrating component contribution.

DM/BU rapidly improved agitation symptoms. DM/BU numerically separated from placebo at Week 2 with a mean reduction from baseline in the CMAI total score of 11.5 points for DM/BU compared to 8.7 points for placebo (p=0.069).

DM/BU demonstrated a statistically significant mean reduction from baseline in the CMAI total score of 13.8 points for DM/BU compared to 9.7 points for placebo at Week 3 (p=0.007), with statistical significance for this measure maintained thereafter.

Figure 4:
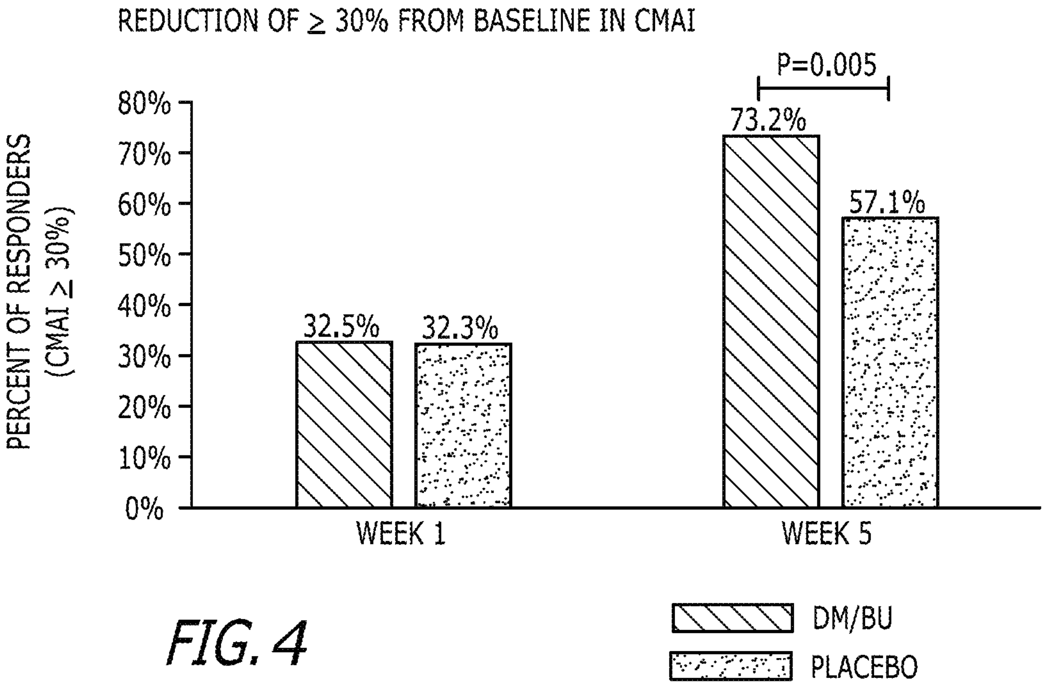
FIG. 4 is a plot of the percentage of responders with CMAI reduction≥30% from baseline over time for the subjects described in Example 5.

As shown in FIG. 4, a statistically significantly greater proportion of patients achieved a clinical response on the CMAI, defined as a 30% or greater improvement from baseline, with DM/BU as compared to placebo (73% versus 57%, p=0.005). These results were consistent with clinicians' global assessments of change measured using the modified Alzheimer's Disease Cooperative Study-Clinical Global Impression of Change for Agitation (mADCS-CGIC). DM/BU demonstrated statistically significantly greater improvement in agitation as compared to placebo on this measure (p=0.036).

DM/BU was safe and well tolerated in the trial. The most commonly reported adverse events in the DM/BU arm were somnolence (8.2% for DM/BU versus 4.1% for bupropion and 3.2% for placebo), dizziness (6.3%, 10.2%, 3.2%, for DM/BU, bupropion, and placebo arms respectively), and diarrhea (4.4%, 6.1%, 4.4%, for DM/BU, bupropion, and placebo arms respectively). The rates of discontinuation due to adverse events were 1.3%, 2.0%, and 1.3% in the DM/BU, bupropion, and placebo arms, respectively. Serious adverse events were reported in 3.1% of patients treated with DM/BU, compared to 8.2% of bupropion, and 5.7% of placebo-treated patients. No serious adverse events were deemed to be related to study drug in any treatment arm. There was one death in the placebo arm, one in the bupropion arm, and none in the DM/BU arm. There was no evidence of cognitive decline for patients treated with DM/BU as shown by the Mini-Mental State Examination (MMSE), a widely utilized measure of general cognitive function. Treatment with DM/BU was not associated with sedation. Adverse events are listed in Table 2 below.

TABLE 2

| Treatment-Emergent Adverse Event | | | |
|---|---|---|---|
| | DM/BU (n = 159) | Bupropion (n = 49) | Placebo (n = 158) |
| Subjects with any TEAE | 70 (44.0%) | 30 (61.2%) | 52 (32.9%) |
| Somnolence | 13 (8.2%) | 2 (4.1%) | 5 (3.2%) |
| Dizziness | 10 (6.3%) | 5 (10.2%) | 5 (3.2%) |
| Diarrhea | 7 (4.4%) | 3 (6.1%) | 7 (4.4%) |
| Headache | 6 (3.8%) | 3 (6.1%) | 5 (2.5%) |
| Falls | 4 (2.5%) | 7 (14.3%) | 3 (1.9%) |
| Fatigue | 3 (1.9%) | 5 (10.2%) | 2 (1.3%) |
| Insomnia | 1 (0.6%) | 3 (6.1%) | 3 (1.9%) |
| Serious AEs | 5 (3.1%) | 4 (8.2%) | 9 (5.7%) |
| Discontinuation due to AEs | 2 (1.3%) | 1 (2.0%) | 2 (1.3%) |
| Deaths | 0 | 1 (2.0% | 1 (0.6%) |

Abbreviations: AE = adverse event;
TEAE = Treatment-emergent adverse event.
Safety Population, data presented as number of subjects (% of subjects).
Treatment-emergent AEs occurring in ≥5% of subjects in any treatment group are presented.

Unless otherwise indicated, all numbers expressing quantities of ingredients, properties such as amounts, percentage, and so forth used in the specification and claims are to be understood in all instances as indicating both the exact values as shown and as being modified by the term "about." Accordingly, unless indicated to the contrary, the numerical parameters set forth in the specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

Use of the term "comprising" or "comprises" herein also contemplates that use of "consisting essentially of," "consists essentially of," "consisting of," or "consists of" in its place.

Affirmative recitation of an element anywhere herein should be understood to contemplate both including and excluding that element.

The terms "a," "an," "the" and similar referents used in the context of describing the embodiments (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the embodiments and does not pose a limitation on the scope of any claim. No language in the specification should be construed as indicating any non-claimed element essential to the practice of the claims.

Groupings of alternative elements or embodiments disclosed herein are not to be construed as limitations. Each group member may be referred to and claimed individually or in any combination with other members of the group or other elements found herein. It is anticipated that one or more members of a group may be included in, or deleted from a group, for reasons of convenience and/or to expedite prosecution. When any such inclusion or deletion occurs, the specification is deemed to contain the group as modified thus fulfilling the written description of all Markush groups if used in the appended claims.

Certain embodiments are described herein, including the best mode known to the inventors for carrying out the claimed embodiments. Of course, variations on these described embodiments will become apparent to those of ordinary skill in the art upon reading the foregoing description. The inventor expects skilled artisans to employ such variations as appropriate, and the inventors intend for the claimed embodiments to be practiced otherwise than specifically described herein. Accordingly, the claims include all modifications and equivalents of the subject matter recited in the claims as permitted by applicable law. Moreover, any combination of the above-described elements in all possible variations thereof is contemplated unless otherwise indicated herein or otherwise clearly contradicted by context.

In closing, it is to be understood that the embodiments disclosed herein are illustrative of the principles of the claims. Other modifications that may be employed are within the scope of the claims. Thus, by way of example, but not of limitation, alternative embodiments may be utilized in accordance with the teachings herein. Accordingly, the claims are not limited to embodiments precisely as shown and described.

The invention claimed is:

1. A method of treating agitation associated with dementia due to Alzheimer's disease in a human patient in need thereof comprising: 1) orally administering with or without food a first dosage form once daily for one week to the human patient, then administering with or without food the first dosage form twice daily to the human patient for one week; and 2) then orally administering with or without food a second dosage form twice daily to the human patient thereafter, for a total of at least five weeks; wherein the human patient is not a CYP2D6 poor metabolizer, and does not have moderate renal impairment; wherein the first and second dosage forms are bilayer tablets;

wherein the first dosage form comprises about 30 mg of dextromethorphan hydrobromide, or a molar equivalent amount of another salt form of dextromethorphan or the free base form of dextromethorphan, about 105 mg of bupropion hydrochloride, or a molar equivalent amount of another salt form of bupropion or the free base form of bupropion, and a polymer; and wherein the second dosage form comprises about 45 mg of dextromethorphan hydrobromide, or a molar equivalent amount of another salt form of dextromethorphan or the free base form of dextromethorphan, and about 105 mg of bupropion hydrochloride, or a molar equivalent amount of another salt form of bupropion or the free base form of bupropion.

2. The method of claim 1, wherein the first or second dosage form further comprises colloidal silicon dioxide.

3. The method of claim 1, wherein the first or second dosage form further comprises crospovidone.

4. The method of claim 1, wherein the first or second dosage form further comprises: glyceryl monocaprylocaprate.

5. The method of claim 1, wherein the first or second dosage form further comprises L-cysteine hydrochloride monohydrate.

6. The method of claim 1, wherein the first or second dosage form further comprises magnesium stearate.

7. The method of claim 1, wherein the first or second dosage form further comprises microcrystalline cellulose.

8. The method of claim 1, wherein the first or second dosage form further comprises polyvinyl alcohol.

9. The method of claim 1, wherein the first or second dosage form further comprises sodium lauryl sulfate.

10. The method of claim 1, wherein the first or second dosage form further comprises stearic acid.

11. The method of claim 1, wherein the first or second dosage form further comprises titanium dioxide.

12. The method of claim 1, wherein the polymer is a carbomer homopolymer.

13. The method of claim 1, wherein the first or second dosage form further comprises: colloidal silicon dioxide, crospovidone, glyceryl monocaprylocaprate, L-cysteine hydrochloride monohydrate, magnesium stearate, microcrystalline cellulose, polyvinyl alcohol, red iron oxide, sodium lauryl sulfate, stearic acid, talc, titanium dioxide, or yellow iron oxide, or a combination thereof.

14. The method of claim 1, wherein the first or second dosage form comprises about 105 mg of bupropion hydrochloride.

15. The method of claim 1, wherein the first dosage form comprises about 30 mg of dextromethorphan hydrobromide.

16. The method of claim 14, wherein the first dosage form comprises about 30 mg of dextromethorphan hydrobromide.

17. The method of claim 1, wherein the second dosage form comprises about 45 mg of dextromethorphan hydrobromide.

18. The method of claim 14, wherein the second dosage form comprises about 45 mg of dextromethorphan hydrobromide.

19. The method of claim 1, wherein the dextromethorphan is formulated for immediate release.

20. The method of claim 19, wherein the bupropion is formulated for extended release.

* * * * *